(12) United States Patent
Torii et al.

(10) Patent No.: US 7,098,284 B2
(45) Date of Patent: Aug. 29, 2006

(54) WATER-ABSORBING AGENT AND PRODUCTION PROCESS THEREFOR, AND WATER-ABSORBENT STRUCTURE

(75) Inventors: Kazushi Torii, Himeji (JP); Toshimasa Kitayama, Himeji (JP); Nobuyuki Harada, Suita (JP)

(73) Assignee: Nippon Shokubal Co., Ltd, Osaka (JP)

( * ) Notice: Subject to any disclaimer, the term of this patent is extended or adjusted under 35 U.S.C. 154(b) by 368 days.

(21) Appl. No.: 10/053,659

(22) Filed: Jan. 24, 2002

(65) Prior Publication Data

US 2003/0069359 A1    Apr. 10, 2003

(30) Foreign Application Priority Data

Jan. 26, 2001 (JP) ............................ 2001-017902
Jun. 12, 2001 (JP) ............................ 2001-176945

(51) Int. Cl.
*C08F 2/10* (2006.01)
(52) U.S. Cl. .................................. 526/317.1; 526/318
(58) Field of Classification Search ............ 526/317.1, 526/318
See application file for complete search history.

(56) References Cited

U.S. PATENT DOCUMENTS

| | | | |
|---|---|---|---|
| 3,888,257 A | 6/1975 | Cook et al. .................. 128/296 |
| 3,935,099 A | 1/1976 | Weaver et al. ................. 210/43 |
| 3,959,569 A | 5/1976 | Burkholder, Jr. ............. 428/475 |
| 4,043,952 A | 8/1977 | Ganslaw et al. ............ 260/17.4 |
| 4,051,086 A | 9/1977 | Reid .................... 260/17.4 GC |
| 4,076,663 A | 2/1978 | Masuda et al. ....... 260/17.4 GC |
| 4,124,748 A | 11/1978 | Fujimoto et al. ............... 526/8 |
| 4,389,513 A | 6/1983 | Miyazaki ..................... 525/186 |
| 4,625,001 A | 11/1986 | Tsubakimoto et al. ......... 526/88 |
| 4,654,039 A | 3/1987 | Brandt et al. ................ 604/368 |
| 4,666,983 A | 5/1987 | Tsubakimoto et al. ...... 525/119 |
| 4,734,478 A | 3/1988 | Tsubakimoto et al. ...... 527/300 |
| 4,755,560 A | 7/1988 | Ito et al. ........................ 525/100 |
| 5,002,986 A | 3/1991 | Fujiura et al. ................. 524/47 |
| 5,164,459 A | 11/1992 | Kimura et al. .............. 525/384 |
| 5,250,640 A | 10/1993 | Irie et al. ....................... 526/88 |
| 5,275,773 A | 1/1994 | Irie et al. ..................... 264/141 |
| 5,281,340 A | 1/1994 | Sato et al. ................... 210/734 |
| 5,382,610 A | 1/1995 | Harada et al. ................. 524/35 |
| 5,409,771 A | 4/1995 | Dahmen et al. ............. 428/327 |
| 5,797,893 A | 8/1998 | Wada et al. .................. 604/372 |
| 5,981,070 A | 11/1999 | Ishizaki et al. .............. 428/407 |
| 5,985,944 A | 11/1999 | Ishizaki et al. ............... 521/64 |
| 6,011,196 A | 1/2000 | Wang et al. ................. 604/368 |
| 6,297,319 B1 | 10/2001 | Nagasuna et al. ............ 525/96 |

FOREIGN PATENT DOCUMENTS

| | | |
|---|---|---|
| DE | 4020780 | 8/1991 |
| EP | 0349240 | 1/1990 |
| EP | 0456136 | 11/1991 |
| EP | 0761241 | 3/1997 |
| EP | 0827753 | 3/1998 |
| EP | 1029886 | 8/2000 |
| JP | 51136588 | 11/1976 |
| JP | 52117393 | 10/1977 |
| JP | 58180233 | 10/1983 |
| JP | 59189103 | 10/1984 |
| JP | 6116903 | 1/1986 |
| JP | 61211305 | 9/1986 |
| JP | 61252212 | 11/1986 |
| JP | 61257235 | 11/1986 |
| JP | 61264006 | 11/1986 |
| JP | 627745 | 1/1987 |
| JP | 2227435 | 9/1990 |
| JP | 531362 | 2/1993 |
| JP | 569159 | 4/1993 |
| JP | 6370 | 1/1994 |
| JP | 853550 | 2/1996 |
| JP | 93123 | 1/1997 |
| JP | 2624089 | 4/1997 |
| JP | 9509591 | 9/1997 |
| JP | 9290000 | 11/1997 |
| JP | 3017584 | 12/1999 |
| JP | 200095955 | 4/2000 |
| JP | 2000197818 | 7/2000 |
| JP | 3107909 | 9/2000 |
| JP | 2000302876 | 10/2000 |
| JP | 2000342963 | 12/2000 |
| WO | 9522356 | 8/1995 |
| WO | WO 95/22355 | 8/1995 |
| WO | WO 95/22358 | 8/1995 |

(Continued)

Primary Examiner—Ana Woodward
(74) Attorney, Agent, or Firm—Roylance, Abrams, Berdo & Goodman, L.L.P.

(57) ABSTRACT

The present invention provides: a novel water-absorbing agent, which exhibits an excellent absorption capacity under a load (AAP), gel layer liquid permeation rate under a load (FRUP), saline flow conductivity (SFC), and shape-maintaining property and ball burst strength (BBS) of a swollen water-absorbing agent aggregate, and excellent persistency of these effects for a long time. The water-absorbing agent, which comprises a polymer obtained by a process including the steps of polymerizing and then crosslinking a monomer including acrylic acid and/or a salt thereof, with the water-absorbing agent being characterized by: (1) exhibiting a free swelling capacity of not less than 23 g/g (GV), a gel deformation of not more than 12.5 cm under a short-time load (0.5 hrPT), and a gel deformation deterioration of not more than 3.5 cm under a load with the passage of time ($\Delta$PT); (2) exhibiting a free swelling capacity of not less than 23 g/g (GV), a ball burst strength of not less than 80 gf (BBS), and a deterioration of ball burst strength of not more than 40% (DBBS); or (3) exhibiting a free swelling capacity of not less than 23 g/g (GV), an absorption capacity of not less than 20 g/g under a load of 4.9 kPa (AAP), and a gel deformation of not more than 12.5 cm under a load (16 hrPT).

26 Claims, 9 Drawing Sheets

FOREIGN PATENT DOCUMENTS

| | | |
|---|---|---|
| WO | 9605234 | 2/1996 |
| WO | 9617884 | 6/1996 |
| WO | 9703114 | 1/1997 |
| WO | 9739780 | 10/1997 |
| WO | 9925393 | 5/1999 |
| WO | 9934841 | 7/1999 |
| WO | 9934842 | 7/1999 |
| WO | 9934843 | 7/1999 |
| WO | 9942494 | 8/1999 |
| WO | 9943720 | 9/1999 |
| WO | 0031153 | 6/2000 |

Water-absorbing agent 1

Before pressurization

After pressurization

Comparative water-absorbing agent 2

Before pressurization

After pressurization

WATER-ABSORBING AGENT AND PRODUCTION PROCESS THEREFOR, AND WATER-ABSORBENT STRUCTURE

BACKGROUND OF THE INVENTION

A. Technical Field

This invention relates to a novel water-absorbing agent, a production process therefor, and a water-absorbent structure.

B. Background Art

In recent years, water-absorbent resins are widely used as constituent materials of water-absorbent articles, such as disposable diapers, sanitary napkins, and so-called incontinent pads, for the purpose of causing the water-absorbent resins to absorb body fluids. Known examples of the above water-absorbent resins are disclosed in Japan Industrial Standard (JIS) K7223-1996. Examples of the known water-absorbent resins include: crosslinked products of partially neutralized polyacrylic acids; hydrolyzed products of starch-acrylic acid graft polymers, saponified products of vinyl acetate-acrylic acid ester copolymers, hydrolyzed products of acrylonitrile- or acrylamide copolymers, and crosslinked products thereof; and crosslinked polymers of cationic monomers.

The water-absorbent resins are hardly used alone because they are generally powders. They are mixed with hydrophilic cellulose fibers, such as pulverized pulps and paper, and used as water-absorbent structures such as disposable diapers (for example, U.S. Pat. No. 3,888,257). When the water-absorbent resins alone are used for absorbing much water in a short time, they cannot absorb in a short time. Therefore, the above mixing is particularly required in order to prevent the water from spreading. The cellulose fibers have functions of: retaining powdery absorbent-reins, or sufficiently spreading water to the water-absorbent resins that are distributed according to capillary action, or retaining swollen water-absorbent resins after water is absorbed.

However, when water-absorbent structures as obtained by the above art are used as disposable diapers, and when the ratio of the absorbent resin particles to the cellulose fibers is higher, the cohesive strength is weak among the cellulose fibers. Therefore, the water-absorbent structures have the following problems: the absorption properties are not as sufficient as expected because the absorbent resins as swollen are moved and dropped after they absorb urine in practical use; and the absorption structures do not display the aimed properties because the decomposition of the absorbent resin particles is caused by a certain kind of component in the urine.

Heretofore, many proposals have been made to solve the above problems. Hereinafter, their artificial contents and problems are described.

JP-A-31362/1993 discloses a method which involves: treating a surface of a water-absorbent resin particle having a carboxyl group with a crosslinking agent having two or more functional groups which can form a covalent bond by reacting with the carboxyl group in order to crosslink with a portion of the carboxyl groups; and thereafter blending the particle with a cationic polymer compound which can form an ionic bond by reacting with the carboxyl group and has a weight-average molecular weight of not less than 2,000.

Japanese Patent No. 3017584 discloses a method for producing a water-absorbent structure, wherein the water-absorbent structure includes a water-absorbent resin particle of which the surface has an acidic group, a cellulose fiber, and a cationic polymer compound having a weight-average molecular weight of not less than 2,000.

U.S. Pat. No. 5,382,610 discloses a method which involves: treating a surface of a water-absorbent resin particle having a carboxyl group with a crosslinking agent having two or more functional groups which can form a covalent bond by reacting with the carboxyl group in order to crosslink with a portion of the carboxyl groups; and thereafter blending the particle with a cationic polymer compound which can form an ionic bond by reacting with the carboxyl group and has a weight-average molecular weight of not less than 2,000, and a method which involves producing a water-absorbent structure which comprises a water-absorbent resin particle of which the surface has an acidic group, a cellulose fiber, and a cationic polymer compound having a weight-average molecular weight of not less than 2,000.

Japanese Patent No. 3107909 discloses a particulate water-absorbing agent having the following properties: the ratio of the particles having particle diameters of not larger than 149 μm is less than 10 weight %; and the water-absorbing agent exhibits an absorption rate of 20 to 90 seconds when 28 g of physiological saline is absorbed in the water-absorbing agent (g), with the water-absorbing agent being characterized in that: when an iron ball (a ball as described in JIS B-1501) having a diameter of $^{15}/_{32}$ inch (about 11.9 cm) freely falls from a point having a height of 20 cm to the swollen hydrogel as obtained in the above way, the iron ball bounds on the swollen hydrogel, or the swollen hydrogel is not invaded by the iron ball (about 11.9 cm) after the iron ball stands still.

JP-A-227435/1990 discloses a liquid-absorbent polymer composition, which comprises a base polymer particle having a absorption rate of not more than 20 seconds, substantially water-absorbency, and an absorption capacity of at least 30 ml/g under an ordinary pressure, and is surface-crosslinked with a multivalent ionic crosslinking agent, and is granulated so that the particle size of the polymer composition will be larger than that of the base polymer particle, with the liquid-absorbent polymer composition being characterized by having the particle distribution such that: the liquid-absorbent polymer particle does not substantially include a particle larger than 300 μm before the liquid-absorbent polymer particle is surface-crosslinked and granulated, and 40% or more of the particles have particle diameters of not larger than 150 μm.

JP-A-53550/1996 discloses a method for producing a high-water-absorbent resin, which involves: adding (a) a hydrophilic polymer and (b) a crosslinking agent into a high-water-absorbent resin hydrogel, wherein the high-water-absorbent resin hydrogel is obtained by adding 10 to 100 parts by weight of water to 100 parts by weight of a high-water-absorbent resin, wherein the hydrophilic polymer has a reactive group and the amount of the hydrophilic polymer is 0.005 to 5 parts by weight per 100 parts by weight of the high-water-absorbent resin, and wherein the crosslinking agent has two or more functional groups reactable with the hydrophilic polymer having the reactive group and the weight ratio of the hydrophilic polymer/crosslinking agent is in the range of 0.1 to 30; blending them together; and carrying out a heating reaction of them.

Water-absorbent resins as modified by these known arts are certainly difficult to move or drop when they are combined with cellulose fibers. In addition, the swollen water-absorbing agent aggregate may also have an excellent shape-maintaining property and ball burst strength (BBS). In the present invention, the "swollen water-absorbing agent aggregate" means a state such that water-absorbing agents as swollen come into contact with one another after absorbing water, and can be regarded as one lump, for example, a state such that the cohesive strength of such as ionic bond, hydrogen bond, covalent bond, and coordinate bond is applied among swollen water-absorbing agents, and the swollen water-absorbing agents come into contact with one another. However, the water-absorbent resin particles and/or water-absorbing agents do not have a sufficient absorption amount of water under a load (absorption capacity under a load (AAP)), gel layer liquid permeation rate under a load (FRUP), saline flow conductivity (SFC). Therefore, when they were combined with cellulose fibers or other materials, the absorption properties could not be said to be sufficient. For example, when the water-absorbing agents were used as a portion of a water-absorbent structure in disposable diapers, they had a low absorption capacity under a load (AAP). Therefore, they had the following serious problems: a demerit such that the urine as absorbed in the water-absorbent structure is returned to the surface of the diaper when the pressure is exerted by body weight; and a demerit such that the water-absorbent structure has a low liquid permeability therein because the gel layer liquid permeation rate under a load (FRUP) and the saline flow conductivity (SFC) are not sufficient, and therefore, the liquid does not spread enough in the water-absorbent structure, and the decrease of the absorption amount of water and the leak of the liquid are caused.

In addition, the above water-absorbent resins as modified by these known arts are certainly difficult to move or drop when they are combined with cellulose fibers. In addition, the swollen water-absorbing agent aggregate may also have an excellent shape-maintaining property and ball burst strength (BBS). However, its absorption properties are gradually lost with the passage of time after it absorbs water, and particularly there was a demerit such that the shape-maintaining property and ball burst strength (BBS) of the swollen water-absorbing agent aggregate were considerably lowered. Because these are lowered, when disposal diapers comprising a water-absorbent resin in a high ratio are especially used for a long time, it results in moving the resultant swollen gel and lowing absorption properties.

WO 97/03114 discloses a method for producing a water-absorbing agent powder, which is characterized by decreasing a residual crosslinking agent by adding a nucleophilic agent to a carboxyl-group-containing water-absorbent resin powder of which the surface neighborhood is surface-crosslinked with a crosslinking agent including an epoxy group and in which the crosslinking agent remains, wherein the water-absorbent resin powder is in a state of heated powder. In Example 1 as described in this document, an example of adding polyethylenimine as a nucleophilic agent to a water-absorbent resin powder is described.

JP-A-509591/1997 and WO 95/22356 disclose an absorbing material having an improved absorbency, which includes a mixture of: (1) two or more absorbent gel-formable particles which are water-insoluble and include a water-swellable polymer; and (2) an absorbency-improved polymer reactable with at least one component included in urine, with the water-absorbing material being characterized in that the mixture is produced by: (i) applying a solution onto the two or more absorbent gel-formable particles, wherein the solution includes an organic solvent (favorably, polar organic solvent), water, and the absorbency-improved polymer, and the weight ratio between the organic solvent and the water is at least 50:50, favorably in the range of 70:30 to 98:2; and (ii) removing a portion of the organic solvent and water from these applied absorbent gel-formable particles. In Examples as described in this document, an example of adding polyallylamine to a water-absorbent resin powder is described.

JP-A-342963/2000 discloses a method for producing an absorbing agent composition, which is characterized by adding a polyamine compound having a weight-average molecular weight of not less than 5,000 to a water-absorbent resin having an diffusive absorption capacity of not less than 25 g/g in an aqueous sodium chloride solution of 0.9 weight % after 60 minutes from the start of swelling under a load of 20 g/cm$^2$ (1.96 kPa).

WO 96/17884 discloses a water-absorbent resin composition having a water-holding ability of not less than 20 g/g, an absorption rate of not more than 120 seconds, a liquid permeation rate of not more than 200 seconds under a load. In Example 19 as described in this document, an example of adding polyethylenimine to a water-absorbent resin particle is described.

JP-A-290000/1997 discloses an absorbing material that comprises (a) an absorbent gel particle including a water-insoluble absorbent hydrogel-formable polymer, (b) a polycationic polymer, (c) a glue fine fiber, and (d) a carrier layer, with the absorbing material being characterized in that the polycationic polymer is bonded to the absorbent gel particle and the glue fine fiber acts as an adhesive agent between the absorbent gel particle and the carrier layer.

Even in these technical arts, the cationic polymer compound as blended with the water-absorbent resin particle is not sufficiently crosslinked, or the gel layer permeation rate under a load (FRUP) or the saline flow conductivity (SFC) of the water-absorbent resin particle is not sufficient. Therefore, the absorption properties could not be said to be sufficient in the same reason as of the above. In addition, as to the swollen water-absorbing agent aggregate, its absorption properties are gradually lost with the passage of time after it absorbs water, and there was particularly a demerit such that the shape-maintaining property and ball burst strength (BBS) of the swollen water-absorbing agent aggregate were considerably lowered.

JP-A-3123/1997 discloses a water-absorbent polymer characterized by displaying a delay bonding character in contact with a water-containing liquid. Even in this technical art, the gel layer permeation rate under a load (FRUP) or the saline flow conductivity (SFC) of a water-absorbent resin particle is not sufficient. Therefore, the absorption properties could not be said to be sufficient in the same reason as of the above. In addition, there was a demerit such that: the absorption capacity of a water-absorbing agent under a load (AAP) was not sufficient wherein the water-absorbing agent was obtained by blending the water-absorbent resin particle and a polyamine together; and the urine as absorbed in a water-absorbent structure was returned to the surface of a diaper when the pressure was exerted by body weight.

WO 97/12575 discloses a technical art to improve a gel layer permeability under a load by carrying out a reaction between a water-insoluble water-absorbing hydrogel-formable polymer and a polycationic polymer, and forming a covalent bond between both of them. However, there was a demerit such that the shape-maintaining property and ball burst strength (BBS) of a swollen water-absorbing agent aggregate were considerably lowered because the covalent bond was formed between both of them by heating. In addition, the gel layer permeation rate under a load (FRUP) or the saline flow conductivity (SFC) of a water-absorbent resin particle is not sufficient. Therefore, the absorption properties could not be said to be sufficient in the same reason as of the above.

In WO 99/34841, WO 99/34842, WO 99/34843, and WO 99/25393, an acidic-group-containing water-insoluble swellable polymer and a basic-group-containing water-insoluble swellable polymer are mixed together and used. Accordingly, when the resultant polymer comes into contact with saline, the salt in the saline is absorbed into the polymer and the respective acid group and base group are neutralized with the salt. Therefore, the following properties are sufficiently generalized: an absorption capacity under a load (AAP), a saline flow conductivity (SFC), and a shape-maintaining property and a ball burst strength (BBS) of a swollen water-absorbing agent aggregate. However, the ratio of the acidic group and the basic group is important in this technical art, and it is very uneconomical because the valuable basic water-insoluble swellable polymer must be used in a large amount (usually, the amount is nearly equal to that of the acidic-group-containing water-insoluble swellable polymer, at least not less than 10 weight %). In addition, there was a demerit such that the absorption amount of water was extremely lowered in a liquid not including salt or in the presence of more salt than the amount possible to neutralize. Furthermore, there was usually a demerit such that the free swelling capacity (GV) of the water-absorbing agent as obtained in the above technical art was not sufficient.

JP-A-95955/2000 discloses a water-absorbing agent composition comprising at least a water-absorbent resin particle having an anionic dissociative group and a water-swellable resin particle having a cationic group, with the water-absorbing agent composition being characterized in that: 45 to 90 mol % of the anionic dissociative groups of the water-absorbent resin particle are neutralized; the weight ratio ($\alpha$) of the water-absorbent resin particle having the anionic dissociative group relative to the total weight of the water-absorbent resin particle having the anionic dissociative group and the water-swellable resin particle having the cationic group is at least 0.8; and the absorption capacity of the water-absorbing agent composition under a load (P) is at least 20 g/g. The water-absorbing agent as obtained by this technical art has a sufficient absorption capacity under a load (AAP) and saline flow conductivity (SFC). However, the water solubility of the water-swellable resin particle having the cationic group as used in this technical art is low. Therefore, there was a demerit such that the shape-maintaining property and ball burst strength (BBS) of a swollen water-absorbing agent aggregate were considerably lowered.

SUMMARY OF THE INVENTION

A. Object of the Invention

The following absorbent resin is ideal when it is practically used: an absorbent resin, which exhibits an excellent absorption capacity under a load (AAP), gel layer liquid permeation fate under a load (FRUP), and saline flow conductivity (SFC), and sufficiently brings out synergism with a partner material to be combined with, such as cellulose fibers, and has an excellent shape-maintaining property or ball burst strength (BBS) of a swollen water-absorbing agent aggregate, and maintains these effects for a long time. However, this has not been obtained yet under the present circumstances.

B. Disclosure of the Invention

As a means of solving the above problems, this invention first provides: a production process for a water-absorbing agent, which comprises the step of blending 100 parts by weight of water-absorbent resin particles (A) and 0.01 to 10 parts by weight of a cationic polymer compound (B) together, wherein the cationic polymer compound (B) is obtained by a process including the step of crosslinking a cationic polymer with a crosslinking agent of which the amount is 0.01 to 10 weight % of the cationic polymer, and wherein the cationic polymer compound (B) has a water solubility of 70 to 10 weight % if the cationic polymer compound (B) is obtained from an ethylenimine monomer, otherwise the cationic polymer compound (B) has a water solubility of 100 to 10 weight %.

The present invention secondly provides: a production process for a water-absorbing agent, which comprises the step of blending 100 parts by weight of water-absorbent resin particles (A) and 0.01 to 10 parts by weight of a cationic polymer compound (B) together, wherein the water-absorbent resin particles (A) exhibit an absorption capacity of not less than 20 g/g under a load of 4.9 kPa (AAP) and a gel layer liquid permeation rate of not more than 800 seconds under a load (FRUP), and wherein the cationic polymer compound (B) has a water solubility of 100 to 10 weight %.

The present invention thirdly provides: a production process for a water-absorbing agent, which comprises the step of blending 100 parts by weight of water-absorbent resin particles (A) and 0.01 to 10 parts by weight of a cationic polymer compound (B) together, wherein the water-absorbent resin particles (A) exhibit an absorption capacity of not less than 20 g/g under a load of 4.9 kPa (AAP) and a saline flow conductivity of not less than 20 ($10^{-7} \times cm^3 \times s \times g^{-1}$) (SFC), and wherein the cationic polymer compound (B) has a water solubility of 100 to 10 weight %.

The present invention fourthly provides: a water-absorbing agent, which is obtained by the production process for a water-absorbing agent according to the present invention.

The present invention fifthly provides: a water-absorbing agent, which comprises water-absorbent resin particles (A) and a cationic polymer compound (B), wherein the cationic polymer compound (B) is substantially ionically bonded to the water-absorbent resin particles (A), with the water-absorbing agent being characterized by exhibiting a free swelling capacity of not less than 23 g/g (GV), an absorption capacity of not less than 20 g/g under a load of 4.9 kPa (AAP), and a saline flow conductivity of not less than 50 ($10^{-7} \times cm^3 \times s \times g^{-1}$) (SFC).

The present invention sixthly provides: a water-absorbing agent, which comprises a polymer obtained by a process including the steps of polymerizing and then crosslinking a monomer including acrylic acid and/or a salt thereof, with the water-absorbing agent being characterized by exhibiting a free swelling capacity of not less than 23 g/g (GV), an absorption capacity of not less than 20 μg under a load of 4.9 kPa (AAP), and a gel deformation of not more than 12.5 cm under a load (16 hrPT).

The present invention seventhly provides: a water-absorbing agent, which comprises a polymer obtained by a process including the steps of polymerizing and then crosslinking a monomer including acrylic acid and/or a salt thereof, with the water-absorbing agent being characterized by exhibiting a free swelling capacity of not less than 23 g/g (GV), an absorption capacity of not less than 20 g/g under a load of 4.9 kPa (AAP), and a 16 hours' ball burst strength of not less than 80 gf (16 hrBBS).

The present invention eighthly provides: a water-absorbing agent, which comprises a polymer obtained by a process including the steps of polymerizing and then crosslinking a monomer including acrylic acid and/or a salt thereof, with the water-absorbing agent being characterized by exhibiting a free swelling capacity of not less than 23 g/g (GV), a gel deformation of not more than 12.5 cm under a short-time load (0.5 hrPT), and a gel deformation deterioration of not more than 3.5 cm under a load with the passage of time (ΔPT).

The present invention ninthly provides: a water-absorbing agent, which comprises a polymer obtained by a process including the steps of polymerizing and then crosslinking a monomer including acrylic acid and/or a salt thereof, with the water-absorbing agent being characterized by exhibiting a free swelling capacity of not less than 23 g/g (GV), a ball burst strength of not less than 80 gf (BBS), and a deterioration of ball burst strength of not more than 40% (DBBS).

The present invention tenthly provides: a water-absorbent structure, which comprises the water-absorbing agent as obtained in the present invention.

These and other objects and the advantages of the present invention will be more fully apparent from the following detailed disclosure.

BRIEF DESCRIPTION OF THE DRAWINGS

FIG. 6 is an upper view of these.

EXPLANATION OF THE SYMBOLS

Figure 1:
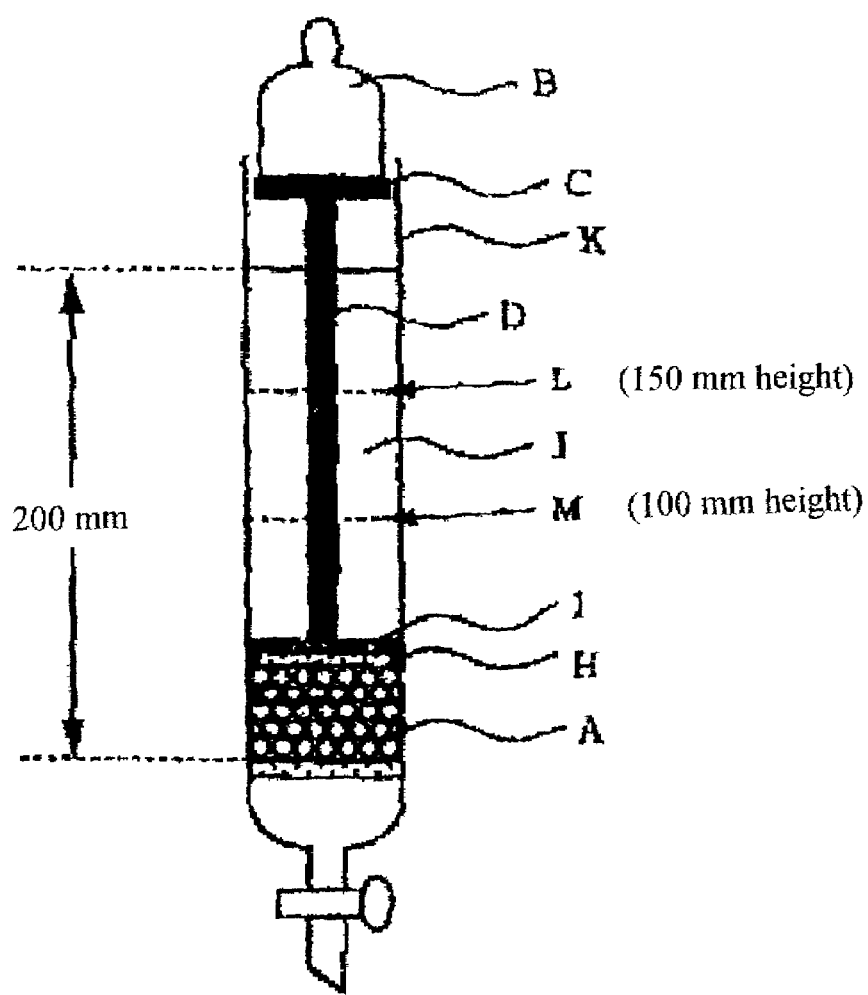
FIG. 1 is a schematic section of a measurement apparatus as used for measuring the gel layer liquid permeation rate under a load (FRUP), which is one of the properties as displayed by the water-absorbent resin particles (A) in the present invention.

A Swollen water-absorbent resin particles
B Weight
C Round plate
D Pressurizing rod
H Glass filter
I Pressurizing plate having glass filter
J Physiological saline
K Glass column having cock
L Standard line (liquid surface having a liquid height of 150 mm)
M Standard line (liquid surface having a liquid height of 100 mm)
1 Round-dish-like (Petri-dish-like) receptacle
2 Swollen water-absorbing agent aggregate
3 Round cover
4 Weight
5 Sealable plastic bag
6 Weight
7 Deformed swollen water-absorbing agent aggregate
8 Straight distance between two points, where the straight distance will be the longest from one arbitrary end to the other arbitrary end
31 Tank
32 Glass tube
33 Aqueous sodium chloride solution of 0.69 weight %
34 L-tube having cock
35 Cock
40 Receptacle
41 Cell
42 Stainless wire mesh
43 Stainless wire mesh
44 Swollen gel
45 Glass filter
46 Piston
47 Holes in piston
48 Collecting receptacle
49 Balance
210 Stainless weight
220 Inner-cylinder cover plate
230 Out-side cylinder
240 Teflon flat-bottomed tray
250 No. 400 mesh stainless-steel screen
260 Water-absorbing agent layer
270 Inner-cylinder
280 Circular lower sample clamp platen
290 Polished stainless steel ball-shaped prove
300 Circular upper sample clamp platen
310 Stationary crosshead
320 Moving crosshead
330 Force sensing load cell

DETAILED DESCRIPTION OF THE INVENTION

Hereinafter, the following abbreviations are used in the explanation of the present invention.

Free swelling capacity: hereinafter, abbreviated to GV.

Absorption capacity under a load of 4.9 kPa: hereinafter, abbreviated to AAP.

Gel layer permeation rate under a load: hereinafter, abbreviated to FRUP.

Saline flow conductivity: hereinafter, abbreviated to SFC.

Gel deformation under a short-time load: hereinafter, abbreviated to 0.5 hrPT.

Gel deformation under a load: hereinafter, abbreviated to 16 hrPT.

Gel deformation deterioration under a load with the passage of time: hereinafter, abbreviated to $\Delta$PT.

Ball burst strength: hereinafter, abbreviated to BBS.

16 hours' ball burst strength: hereinafter, abbreviated to 16 hrBBS.

Deterioration of ball burst strength: hereinafter, abbreviated to DBBS.

In the above, abbreviations, GV is an acronym of Gel Volume, and AAP is an acronym of Absorbency Against Pressure, and FRUP is an acronym of Flow Rate Under Pressure, and SFC is an acronym of Saline Flow Conductivity, and PT is an acronym of Pressure Test, and BBS is an acronym of Ball Burst Strength, and DBBS is an acronym of Deterioration of Ball Burst Strength.

Incidentally, these values are measured according to measurement methods as shown below.

The present invention relates to a water-absorbing agent from a water-absorbent resin, a production process therefor, and a water-absorbent structure. Incidentally, the water-absorbing agent in the present invention means a modified polymer water-absorbing agent comprising a major proportion of a water-absorbent resin (favorably in the range of not less than 70 weight %, more favorably in the range of not less than 80 weight %), or its composition. The water-absorbent resin is a gel-formable resin that has crosslinking structure, and is water-insoluble, and includes a water-swellable polymer.

-Water-Absorbent Resin Particles (A)-

Hereinafter, the water-absorbent resin particles (A), which are used in the present invention, are explained in the first place.

The water-absorbent resin particles (A) usable in the present invention favorably exhibit an AAP of not less than 20 g/g, more favorably not less than 22 g/g, still more favorably not less than 25 g/g, yet still more favorably not less than 27 g/g, most favorably not less than 30 g/g. When the AAP is not less than 20 g/g, and when the water-absorbing agent according to the present invention is partially used as a water-absorbent structure of disposable diapers, the urine as absorbed in the water-absorbent structure is very effectively prevented from returning to the surface of the diaper.

In addition, the water-absorbent resin particles (A) favorably exhibit a FRUP of not more than 1,500 seconds, more favorably not more than 1,200 seconds, still more favorably not more than 800 seconds, yet still more favorably not more than 500 seconds, particularly favorably not more than 300 seconds, most favorably not more than 150 seconds. In addition, the water-absorbent resin particles (A) favorably exhibit a SFC of not less than 20 ($10^{-7} \times cm^3 \times s \times g^{-1}$), more favorably not less than ($10^{-7} \times cm^3 \times s \times g^{-1}$), still more favorably not less than 35 ($10^{-7} \times cm^3 \times s \times g^{-1}$) yet still more favorably not less than 50 ($10^{-7} \times cm^3 \times s \times g^{-1}$), most favorably not less than 75 ($10^{-7} \times cm^3 \times s \times g^{-1}$). The FRUP and SFC of the water-absorbent resin particles (A) have a great influence on liquid permeability of the water-absorbing agent as obtained in the present invention after the water-absorbing agent is swollen. That is to say, if the water-absorbing agent according to the present invention is produced and favorably the FRUP of the water-absorbent resin particles (A) is adjusted to not more than 1,500 seconds and/or the SFC of the water-absorbent resin particles (A) is adjusted to not less than 20 ($10^{-7} \times cm^3 \times s \times g^{-1}$), the following effects are remarkably improved: when the water-absorbing agent according to the present invention is partially used as a water-absorbent structure of disposable diapers, the liquid permeability is improved, and the liquid spreads enough in the water-absorbent structure, and the absorption amount of water is increased, and the leak of the liquid is prevented.

The water-absorbent resin particles (A) favorably used in the present invention, for example, can be produced by carrying out a specific surface-crosslinking treatment in the neighborhood of the particle of a water-absorbent resin (hereinafter, referred as simply "water-absorbent resin") that is a precursor.

Examples of the water-absorbent resin include at least one kind selected from the group consisting of: partially-neutralized and crosslinked poly(acrylic acids); hydrolyzed graft polymers of starch-acrylonitrile; hydrolyzed graft polymers of starch-acrylic acid; saponified copolymers of vinyl acetate-acrylic acid ester; and hydrolyzed copolymers of acrylonitrile or acrylamide, or crosslinked polymers of these hydrolyzed copolymers thereof; modified products of crosslinked poly(vinyl alcohol) including a carboxyl group; and copolymers of crosslinked isobutylene-maleic anhydride. These water-absorbent resins can be used either alone respectively or in combinations with each other. Among these, the water-absorbent resins having a carboxyl group are favorable either alone respectively or in combinations with each other. The water-absorbent resins typically comprise a major proportion of polymers obtained by a process including the step of polymerizing and then crosslinking monomers including acrylic acid and/or its salt (neutralized product) as a main component. Examples thereof are disclosed in the following way: partially-neutralized and crosslinked poly(acrylic acids) (U.S. Pat. No. 4,625,001, U.S. Pat. No. 4,654,039, U.S. Pat. No. 5,250,640, U.S. Pat. No. 5,275,773, and EP 456136); crosslinked and partially-neutralized graft polymers of starch-acrylic acid (U.S. Pat. No. 4,076,663); copolymers of isobutylene-maleic acid (U.S. Pat. No. 4,389,513); saponified copolymers of vinyl acetate-acrylic acid (U.S. Pat. No. 4,124,748); hydrolyzed (co)polymers of acrylamide (U.S. Pat. No. 3,959,569); and hydrolyzed polymers of acrylonitrile (U.S. Pat. No. 3,935,099).

In addition, the above water-absorbent resin as used has a crosslinking structure, and favorably exhibits an uncrosslinked water-extractable content of not more than 25 weight %, more favorably not more than 20 weight %, still more favorably not more than 15 weight %, particularly favorably not more than 10 weight %.

Acrylic acid (salt), namely, acrylic acid and/or its salt (neutralized product) is favorably used as a component comprised in the above water-absorbent resin. Examples of the acrylic acid salt include: acrylic acid salts of alkaline metal, such as sodium, potassium, and lithium; acrylic acid ammonium salts, and acrylic acid amine salts. The acrylic acid sodium salt is favorable. The constituent units of a major proportion of the above water-absorbent resin favorably comprise acrylic acid in the range of 0 to 50 mol % and a salt thereof in the range of 100 to 50 mol % (wherein the total of them is 100 mol %), and more favorably comprise acrylic acid in the range of 10 to 40 mol % and a salt thereof in the range of 90 to 60 mol % (wherein the total of them is 100 mol %). The neutralization of the water-absorbent resin to form the salt may be carried out in a state of monomers before polymerization, or in a state of polymers in the course of or after polymerization, or in combinations of each other. When the neutralization is carried out in a state of polymers, there are advantages in decreasing the water-extractable content. However, it takes fairly much time to carry out the neutralization. Therefore, it is favorable that the neutralization is carried out in a state of monomers before polymerization in view of production costs.

The monomers to obtain the water-absorbent resin as used in the present invention may comprise other monomers in addition to the acrylic acid (salt) when the occasion demands. The monomers other than the acrylic acid (salt) are not especially limited, but examples thereof include: anionic unsaturated monomers, such as methacrylic acid, maleic acid, vinylsulfonic acid, styrenesulfonic acid, 2-(meth)acrylamido-2-methylpropanesulfonic acid, 2-(meth)acryloylethanesulfonic acid, and 2-(meth)acryloylpropanesulfonic acid, and their salts; nonionic unsaturated monomers containing a hydrophilic group, such as acrylamide, methacrylamide, N-ethyl(meth)acrylamide, N-n-propyl(meth)acrylamide, N-isopropyl(meth)acrylamide, N,N-dimethyl(meth)acrylamide, 2-hydroxyethyl (meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloylpiperidine, N-acryloylpyrrolidine, and N-vinylacetamide; cationic unsaturated monomers such as N,N-dimethylaminoethyl (meth)acrylate, N,N-diethylaminoethyl (meth)acrylate, N,N-dimethylaminopropyl (meth)acrylate, N,N-dimethylaminopropyl(meth)acrylamide, and their quaternary salts. These monomers may be used either alone respectively or in combinations with each other.

In the present invention, when the monomers other than the acrylic acid (salt) are used, the ratio is favorably not more than 30 mol %, more favorably not more than 10 mol %, of the total amount of the acrylic acid and its salt. If the above monomers other than acrylic acid (salt) are used in the above ratio, then the absorption properties of the resultant water-absorbent resin (A) are still more improved, and the water-absorbent resin (A) can be obtained at a still lower cost.

When the above monomers are polymerized in order to obtain the water-absorbent resin as used in the present invention, the bulk polymerization or precipitation polymerization can be carried out. However, in view of the performance or the easiness of the polymerization control and further the liquid permeability of swollen gels, the aqueous solution polymerization or reversed-phase suspension polymerization is favorably carried out using the above hydrophilic monomer in the form of its aqueous solution. Incidentally, when the monomer is used in the form of its aqueous solution, the concentration of the monomer in its aqueous solution (hereinafter referred to as "aqueous monomer solution") depends upon the temperature of the aqueous solution or the monomer, and is not especially limited, but is favorably in the range of 10 to 70 weight %, more favorably 20 to 60 weight %. In addition, when the above aqueous solution polymerization is carried out, solvents other than water may be jointly used if necessary, and the kind of the solvents as jointly used is not especially limited.

Examples of the method of the aqueous solution polymerization include: a method that involves polymerizing an aqueous monomer solution in a double-arm type kneader while the resultant hydrogel is pulverized; and a method that involves supplying an aqueous monomer solution into a determined vessel or onto a moving belt and pulverizing the resultant gel from polymerization with such as a meat chopper.

When the above polymerization is initiated, the following radical polymerization initiators, for example, can be used: radical polymerization initiators, such as potassium persulfate, ammonium persulfate, sodium persulfate, t-butyl hydroperoxide, hydrogen peroxide, and 2,2'-azobis(2-amidinopropane) dihydrochloride; and photopolymerization initiators such as 2-hydroxy-2-methyl-1-phenyl-propane-1-one. Furthermore, redox initiators are also available by using reductants together to promote decomposition of the above polymerization initiator and combining both with each other. Examples of the above reductants include: (bi)sulfurous acid (or its salts) such as sodium sulfite and sodium hydrogensulfite; L-ascorbic acid (or its salts); reducible metals (or their salts) such as ferrous salts; and amines. However, the reductants are not especially limited thereto.

The amount of these polymerization initiators as used is in the range of usually 0.001 to 2 mol %, preferably 0.01 to 0.1 mol %. In the case where the amount of these polymerization initiators is less than 0.001 mol %, there are disadvantages in that the amount of unreacted monomers is increased, and therefore the residual amount of the monomers is increased in the resultant water-absorbent resin. On the other hand, in the case where the amount of these polymerization initiators is more than 2 mol %, there may be disadvantages in that the water-extractable content in the resultant polymer is increased.

In addition, the polymerization reaction may be initiated by irradiating the reaction system with active energy rays, such as radiations, electron beam, and ultraviolet rays, and further using the polymerization initiators together. Incidentally, the reaction temperature is not especially limited in the above polymerization reaction, but is preferably in the range of 15 to 130° C., more preferably 20 to 110° C. In addition, the reaction time is not especially limited either, and may fitly be determined according to factors such as the respective kinds of the hydrophilic monomers and polymerization initiators and the reaction temperature.

The above water-absorbent resin may be a self-crosslinking type resin using no crosslinking agent, but is favorably obtained by copolymerizing or reacting with an internal-crosslinking agent that has two or more polymerizable unsaturated groups or two or more reactive groups per a molecule.

Examples of these internal-crosslinking agents include: N,N'-methylenebis(meth)acrylamide, (poly)ethylene glycol di(meth)acrylate, (poly)propylene glycol di(meth)acrylate, trimethylolpropane tri(meth)acrylate, glycerol tri(meth)acrylate, glycerol acrylate methacrylate, ethylene-oxide-modified trimethylolpropane tri(meth)acrylate, pentaerythritol hexa(meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether, ethylene glycol, polyethylene glycol, propylene glycol, glycerol, pentaerythritol, ethylenediamine, ethylene carbonate, propylene carbonate, and glycidyl (meth)acrylate.

These internal-crosslinking agents may be used either alone respectively or in combinations with each other. In addition, these internal-crosslinking agents may be added to the reaction system either all at once or divisionally. When at least one kind or two kinds of internal-crosslinking agents are used, it is favorable to essentially use a compound having two or more polymerizable unsaturated groups in consideration of the absorption properties of the resultant water-absorbent resin.

The amount of the above internal-crosslinking agent as used is in the range of favorably 0.005 to 2 mol %, more favorably 0.02 to 0.5 mol %, still more favorably 0.04 to 0.2 mol %, of the above monomers. In the case where the amount of the internal-crosslinking agent is less than 0.005 mol % and the amount of the internal-crosslinking agent is more than 2 mol %, the water-absorbent resin having sufficient water absorption properties might not be obtained.

When the crosslinking structure is introduced into the internal portion of the water-absorbent resin using the above internal-crosslinking agent, the internal-crosslinking agent may be added to the reaction system before, during or after polymerization of the above monomers, or after neutralization.

Incidentally, in the above polymerization, the following materials may be added to the reaction system: various foaming agents, such as carbonates (or hydrogencarbonates), carbon dioxide, azo compounds, and inert organic solvents; hydrophilic polymers, such as starch cellulose, their derivatives, polyvinyl alcohol, polyacrylic acid (or its salts), and crosslinked products of polyacrylic acid (or its salts); various surfactants; chelating agents; and chain transfer agents such as hypophosphorous acid (or its salts). In addition, inorganic powders may also be added thereto.

When the above crosslinked polymer is obtained by the aqueous solution polymerization and is a gel, namely, a crosslinked hydrogel polymer, the crosslinked polymer is dried, if necessary, and usually pulverized before and/or after drying in order to produce a water-absorbent resin. In addition, the drying is carried out at a temperature of usually 60 to 250° C., favorably 100 to 220° C., more favorably 120 to 200° C., and the drying time is in the range of 10 minutes to 12 hours, favorably 20 minutes to 6 hours, more favorably 30 minutes to 3 hours.

The water content of the water-absorbent resin usable in the present invention is not especially limited, but is favorably in the range of 0 to 400 weight %, more favorably 0.2 to 40 weight %, still more favorably 0.2 to 10 weight %.

In addition, the water-absorbent resin usable in the present invention, for example, is a pulverized one. The water-absorbent resin, which has a weight-average particle diameter of larger than 1,000 µm when the water-absorbent resin is a gel obtained by the polymerization reaction before drying and pulverization, can be used. However, the weight-average diameter is usually in the range of 10 to 1,000 µm, favorably 100 to 800 µm, more favorably 150 to 700 µm (but not including 150 µm), still more favorably 300 to 600 µm (but not including 300 µm), most favorably 400 to 500 µm (but not including 400 µm). Furthermore, the water-absorbent resin favorably contains little fine particle (for example, not larger than 149 µm), for example, in an amount of not more than 10 weight %, favorably not more than 5 weight %, particularly favorably not more than 3 weight %. The particle shape of the water-absorbent resin as obtained in the above way, for example, may be spherical, pulverized, or irregular, and is not especially limited. However, those having irregular pulverized shapes as obtained via the pulverization step are preferably used.

In addition, the water-absorbent resin particles (A) as used in the present invention are favorably obtained by a process including the step of crosslinking the surface neighborhood of the water-absorbent resin as obtained by the above method with a specific surface-crosslinking agent when the occasion demands. Preferred examples of the surface-crosslinking agent as used in the present invention include a compound having at least two functional groups reactable with a functional group in the water-absorbent resin. The functional group in the water-absorbent resin is favorably an anionic dissociative group, more favorably a carboxyl group.

Examples of these surface-crosslinking agents include: polyhydric alcohol compounds such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol and sorbitol; epoxy compounds such as ethylene glycol diglycidyl ether, polyethylene diglycidyl ether, glycerol polyglycidyl ether, diglycerol polyglycidyl ether, polyglycerol polyglycidyl ether, propylene glycol diglycidyl ether, polypropylene glycol diglycidyl ether and glycidol; polyamine compounds, such as ethylenediamine, diethylenetriamine, triethylenetetramine, tetraethylenepentamine, pentaethylenehexamine and polyethylenimine, and their inorganic or organic salts (for example, azetidinium salts); polyisocyanate compounds such as 2,4-tolylene diisocyanate and hexamethylene diisocyanate; polyoxazoline compounds such as 1,2-ethylenebisoxazoline; alkylene carbonate compounds such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxopan-2-one; haloepoxy compounds, such as epichlorohydrin, epibromohydrin and α-methylepichlorohydrin, and their polyamine adducts (for example, Kymene produced by Hercules: registered trademark); silane coupling agents such as γ-glycidoxypropyltrimethoxysilane and γ-aminopropyltriethoxysilane; and polyvalent metallic compounds such as hydroxides and chlorides of zinc, calcium, magnesium, aluminum, iron and zirconium. In addition, examples of the usable surface-crosslinking agent are disclosed in JP-A-180233/1983, JP-A-16903/1986, JP-A-189103/1984, JP-A-117393/1977, JP-A-136588/1976, JP-A-257235/1986, JP-A-7745/1987, JP-A-211305/1986, JP-A-252212/1986, JP-A-264006/1986, DE 4020780, WO 99/42494, WO 99/43720, WO 00/31153, and JP-A-197818/2000. These can be used either alone respectively or in combinations with each other.

In addition, the amount of these surface-crosslinking agents as used is in the range of about 0.001 to 10 parts by weight, favorably 0.01 to 5 parts by weight, relative to 100 parts by weight of the water-absorbent resin particles. In the case where the amount is more than 10 parts by weight, there are disadvantages in that not only it is uneconomical because the suitable properties are not caused but also the residual amount of the surface-crosslinking agent is increased. Furthermore, in the case where the amount of the surface-crosslinking agent as used is less than 0.001 part by weight, there are disadvantages in that the absorption capacity under a load is not improved enough.

In addition, inorganic acids and organic acids may also be used in order to further accelerate the reaction of the surface-crosslinking agent and to further improve the absorption properties. Examples of these inorganic acids and organic acids include sulfuric acid, phosphoric acid, hydrochloric acid, citric acid, glyoxylic acid, glycolic acid, glycerophosphoric acid, glutaric acid, cinnamic acid, succinic acid, acetic acid, tartaric acid, lactic acid, pyruvic acid, fumaric acid, propionic acid, 3-hydroxypropionic acid, malonic acid, butyric acid, isobutyric acid, imidionoacetic acid, malic acid, isethionic acid, citraconic acid, adipic acid, itaconic acid, crotonic acid, oxalic acid, salicylic acid, gallic acid, sorbic acid, gluconic acid, and p-toluenesulfonic acid. The amount of these as used is varied according to pH of the water-absorbent resin, but it is favorably in the range of 0 to 10 parts by weight, more favorably 0.1 to 5 parts by weight, relative to 100 parts by weight of the water-absorbent resin.

When the water-absorbent resin and the surface-crosslinking agent are blended together in the present invention, water is favorably used as a solvent. The amount of the water as used depends upon the kind or particle diameter of the water-absorbent resin, but is favorably more than 0 and not more than 20 parts by weight, more favorably in the range of 0.5 to 10 parts by weight, still more favorably 0.5 to 5 parts by weight, relative to 100 parts by weight of the solid content of the water-absorbent resin.

In addition, when the water-absorbent resin and the surface-crosslinking agent are blended together, a hydrophilic organic solvent may also be used as the solvent if necessary. Examples of the hydrophilic organic solvent include: lower alcohols, such as methyl alcohol, ethyl alcohol, n-propyl alcohol, isopropyl alcohol, n-butyl alcohol, isobutyl alcohol, and t-butyl alcohol; ketones such as acetone; ethers, such as dioxane, tetrahydrofuran, and alkoxypolyethylene glycol; amides such as N,N-dimethylformamide; and sulfoxides such as dimethyl sulfoxide. The amount of the hydrophilic organic solvent as used depends upon the kind or particle diameter of the water-absorbent resin, but it is favorably not more than 20 parts by weight, more favorably not more than 10 parts by weight, still more favorably not more than 5 parts by weight, relative to 100 parts by weight of the solid content of the water-absorbent resin.

Then, when the water-absorbent resin and the surface-crosslinking agent are blended together, for example, the water-absorbent resin is dispersed in the above hydrophilic organic solvent, and thereafter the surface-crosslinking agent may be added thereto. However, the following adding method is favorable: the method comprises the step of directly spraying or dropping the surface-crosslinking agent to the water-absorbent resin while being stirred, wherein the surface-crosslinking agent is dissolved or dispersed in water and/or the hydrophilic organic solvent when the occasion demands. In addition, when water is used for the blending, a water-insoluble inorganic fine particle powder or a surfactant may be allowed to coexist. Examples of the surfactant and water-insoluble inorganic fine particle powder as used are described in U.S. Pat. No. 5,164,459, EP 827753, EP 349240, and EP 761241.

The blending apparatus, which is used when the water-absorbent resin and the surface-crosslinking agent are blended together, has favorably a great blending force in order to blend both materials uniformly and surely. Examples thereof favorably include cylinder type blenders, double-wall cone type blenders, V-character-shaped blenders, ribbon type blenders, screw type blenders, fluidized-furnace rotary disk type blenders, gas current type blenders, double-arm type kneaders, internal blenders, pulverizing type kneaders, rotary blenders, screw type extruders.

After the water-absorbent resin and the surface-crosslinking agent are blended together, the heat treatment and/or photo-irradiation treatment of the resultant mixture is carried out. Accordingly, the neighboring surface of the water-absorbent resin is crosslinked, and the AAP, FRUP, and SFC are favorably adjusted to the above range. When the heat treatment is carried out in the present invention, the treatment time is favorably in the range of 1 to 180 minutes, more favorably 3 to 120 minutes, still more favorably 5 to 100 minutes. The treatment temperature is favorably in the range of 60 to 250° C., more favorably 100 to 210° C., still more favorably 120 to 200° C. In the case where the treatment temperature is lower than 60° C., not only the lowering of the productivity is caused because it takes much time to carry out the heat treatment, but also the aimed water-absorbent resin particles (A) may not be obtained because the uniform crosslinking is not performed. In addition, in the case where the treatment temperature is higher than 250° C., the resultant water-absorbent resin is damaged and therefore there are cases where the water-absorbent resin excellent in absorption capacity cannot be obtained.

The above heat treatment can be carried out with a conventional dryer or furnace. Examples of the dryer include channel type blending dryers, rotary dryers, disk dryers, fluidized-bed dryers, gas-stream type dryers, and infrared dryers. When the photo-irradiation treatment is carried out instead of the heat treatment in the present invention, the irradiation with ultraviolet ray is favorably carried out. In addition, photopolymerization initiators can be used.

The water content of the water-absorbent resin particles (A) usable in the present invention is not especially limited, but it is favorably in the range of 0 to 400 weight %, more favorably 0.01 to 40 weight %, still more favorably 0.1 to 10 weight %.

In addition, particles having a weight-average particle diameter of larger than 1,000 μm can also be used as the water-absorbent resin particles (A) usable in the present invention. However, the weight-average particle diameter is generally in the range of 10 to 1,000 μm, favorably 100 to 800 μm, more favorably 150 to 750 μm, still more favorably 300 to 650 μm (but excluding 300 μm), most favorably 400 to 600 μm (but excluding 400 μm). Furthermore, it is favorable that the amount of fine particles (for example, not larger than 149 μm) in the water-absorbent resin particles (A) is little. For example, the amount is favorably not more than 10 weight %, more favorably not more than 5 weight %, still more favorably not more than 3 weight %.

In addition, particles having a bulk density of less than 0.4 g/ml can also be used, as the water-absorbent resin particles (A) usable in the present invention. The bulk density is favorably not less than 0.4 g/ml, more favorably not less than 0.5 g/ml (the measurement method for the bulk density is described in EP 1029886). In the case where the bulk density is not more than 0.4 g/ml, the water-absorbent resin particles (A) are damaged by a process and therefore the properties thereof may be worse.

The water-absorbent resin particles (A) as obtained in the above way favorably have the above AAP, FRUP, SFC, average particle diameter, bulk density, water extractable content, structure, shape, and water content, but the water-absorbent resin particles (A) according to the present invention can be obtained by other methods.

-Cationic Polymer Compound (B)-

Hereinafter, the cationic polymer compound (B), which is blended with the water-absorbent resin particles (A), is explained in the following.

The cationic polymer compound (B) usable in the present invention has a water solubility of 100 to 10 weight %, favorably 100 to 20 weight %, more favorably 100 to 30 weight %. In the case where the water solubility is less than 10 weight %, the shape-maintaining property or BBS of the swollen water-absorbing agent aggregate, which is one characteristic of the water-absorbing agent in the present invention, may be lowered, or this effect may not be maintained for a long time in addition. Incidentally, the water solubility is obtained by measurement according to the following method.

When the cationic polymer compound (B) and the water-absorbent resin particles (A) are blended together in the present invention, the cationic polymer compound (B) is crosslinked in order that the water solubility will be favorably adjusted in the range of 100 to 10 weight %, more favorably 100 to 20 weight %, still more favorably 100 to 30 weight %. In this case, the cationic polymer compound (B) is favorably obtained by a process including the step of crosslinking a cationic polymer with a crosslinking agent. The amount of the crosslinking agent as used is favorably in the range of 0.01 to 10 weight % relative to the cationic polymer (namely, in the range of 0.01 to 10 parts by weight relative to 100 parts by weight of the cationic polymer), more favorably 0.05 to 7.5 weight %, still more favorably 0.1 to 5 weight %. In the case where the amount is less than 0.01 weight %, the effect of the crosslinking cannot be obtained. In addition, in the case where the amount is more than 10 weight %, the water solubility of the cationic polymer compound (B) may be exceedingly lowered.

Especially, when the cationic polymer compound (B) as used is a polymer obtained from an ethylenimine monomer (namely, a polymer obtained from monomers of which the major proportion comprise an ethylenimine monomer (in the range of not leas than 50 weight %, favorably not leas than 70 weight %)), the water solubility is favorably in the range of 70 to 10 weight %, more favorably 50 to 10 weight %. In the case where the water solubility is more than 70%, there are cases where the water-absorbing agent as obtained has insufficient properties and the water absorption properties of the water-absorbing agent may be lost with the passage of time after water is absorbed, because it is not sufficiently crosslinked. In the case where the water solubility is less than 10 weight %, the effect as expected might not be obtained.

When blending with the water-absorbent resin particles (A) which exhibit an AAP of not less than 20 g/g and a FRUP of not more than 800 seconds or the water-absorbent resin particles (A) which exhibit an AAP of not less than 20 g/g and a SFC of not less than 20 ($10^{-7} \times cm^3 \times s \times g^{-1}$), and when the water solubility of the cationic polymer compound (B) as used is less than 10 weight %, the effect as expected might not be obtained. In this case, the cationic polymer compound (B) is, for example, favorably obtained by a process including the step of crosslinking a cationic polymer with a crosslinking agent. The cationic polymer compound (B), which is crosslinked with the crosslinking agent of which the amount is 0.01 to 10 weight % relative to the cationic polymer, is more favorable. However, in this case, it is not always necessary that the cationic polymer compound (B) is crosslinked.

It is necessary that the amount of the cationic polymer compound (B) as used is in the range of 0.01 to 10 parts by weight, favorably 0.05 to 5 parts by weight, more favorably 0.1 to 3 parts by weight, relative to 100 parts by weight of water-absorbent resin particles (A). Depending upon the particle diameters of the water-absorbent resin particles, in the case where the amount is less than 0.01 part by weight, there are cases where the modification of the water-absorbent resin is insufficient. In the case where the amount is more than 10 parts by weight, there are cases where the effect cannot be obtained in proportion to the amount as added. In addition, there are also disadvantages in economy.

When the above conditions are satisfied, the sinking of the cationic polymer compound (B) into the water-absorbent resin particles (A) can be prevented, and therefore, the following can be prevented: the water absorption properties are lost and the shape-maintaining property and BBS of the swollen water-absorbing agent aggregate are worse with the passage of time.

The cationic polymer compound (B) is used, for example, in a form of powder, aqueous solution, gel-like liquid, or gel-like solid, or in a dissolving form in a mixed solvent obtained from water and a hydrophilic organic solvent such as ethanol, or in a gel form including a mixed solvent obtained from water and a hydrophilic organic solvent such as ethanol. It is not especially limited how the cationic polymer compound (B) is used, but the cationic polymer compound (B) is favorably used in a form of aqueous solution or gel-like liquid.

When the cationic polymer compound (B) is added especially in a form of aqueous solution, the concentration is not especially limited, but it is favorably in the range of 1 to 50 weight %, more favorably 2 to 30 weight %.

The cationic polymer compound (B), which includes at least one selected from the group consisting of primary amino groups, secondary amino groups, tertially amino groups, their salts, and quaternary alkylammonium salts, is favorably used. In this case, the salts of the amino groups are obtained by a neutralization of amino group nitrogen with an inorganic acid or an organic acid, or by a reaction between amino group nitrogen and an electrophilic reagent. Examples of the inorganic acid usable for the neutralization include: carbonic acid; boric acid; hydrogen acids such as hydrochloric acid and hydrofluoric acid; oxygen acids such as sulfuric acid, sulfurous acid, nitric acid, nitrous acid, phosphoric acid, hypophosphorous acid, phosphorous acid, orthophosphoric acid, metaphosphoric acid, polyphosphoric acids (for example, pyrophosphoric acid), tripolyphosphoric acid, ultraphosphoric acid (acidic metaphosphoric acid), and perchloric acid; salts of the above oxygen acids. Examples of the organic acid include acidic-functional-group-containing compounds, such as carboxylic acids, sulfinic acids, sulfonic acids, phenolic acids, enols (tautomers of carbonyl compounds), mercaptans, imides (acid imides), oximes, and sulfonamides. Examples thereof include: hydroxy acids, such as formic acid, acetic acid, propionic acid glycol acid, lactic acid, trichlorolactic acid, glyceric acid, malic acid, tartaric acid, citric acid, tartronic acid, and gallic acid; amino acids such as aspartic acid; and p-toluenesulfonic acid. Examples of the usable electrophilic reagent include: alkyl halides, such as methyl iodide, ethyl iodide, 2-iodopropane, benzyl iodide, methyl bromide, ethyl bromide, 2-bromopropane, benzyl bromide, methyl chloride, ethyl chloride, 2-chloropropane, and benzyl chloride; and alkyl sulfates, such as diethyl sulfate, and dimethyl sulfate. The above inorganic acid, organic acid, and electrophilic reagent are used either alone respectively or in combinations with each other.

Examples of the cationic polymer compound (B) are cationic polyelectrolytes, such as polyethylenimine, polyamines, modified polyamide amines obtained by a graft reaction of ethylenimine, protonated polyamide amines, condensated products between polyamide amines and epichlorohydrin, condensated products between amines and epichlorohydrin, poly(vinylbenzyldialkylammoniums), poly (diallylalkylammoniums), poly(2-hydroxy-3-methacryloyloxypropyldialkylamines), polyether amines, polyvinylamines, modified polyvinylamines, partially hydrolyzed poly(N-vinylformamides), partially hydrolyzed poly(N-vinylalkylamides), partially hydrolyzed (N-vinylformamide)-(N-vinylalkylamide) copolymers, polyalkylamines, polyvinylimidazoles, polyvinylpyridines, polyvinylimidazolines, polyvinyltetrahydropyridines, poly(dialkylaminoalkyl vinyl ethers), poly(dialkylaminoalkyl(meth)acrylates), polyallylamines, polyamidines, cationated starch or cellulose, salts thereof, or reaction products of the above cationic polyelectrolytes with electrophilic reagents. The polyamidines as mentioned herein are polymers having an amidine ring in a molecule, and is favorably obtained by a process including the steps of: copolymerizing N-vinylformamide and acrylonitrile, and thereafter carrying out an acid treatment. Examples of the polyamidines include cationic polymers having an amidine structure as described in Japanese Patent No. 2624089, but the polyamidines are not limited thereto. Among these, it is favorable that the cationic polymer compound (B) includes at least one member selected from the group consisting of polyamidines, polyvinylamines or salts thereof, and partially hydrolyzed poly(N-vinylformamides) or salts thereof.

The cationic polymer compound (B) according to the present invention favorably has a weight-average molecular weight of not less than 2,000, more favorably a number-average molecular weight of not less than 2,000, still more favorably a weight-average molecular weight of not less than 5,000, yet still more favorably a number-average molecular weight of not less than 5,000, most favorably a weight-average molecular weight of not less than 10,000. In the case where the weight-average molecular weight is less than 2,000, the effect as expected might not be obtained. Incidentally, as to the measurement of the average molecular weight, the number-average molecular weight is measured according to viscosity method, and the weight-average molecular weight is measured according to balanced sedimentation method. In addition, it is also measured by other methods such as gel permeation chromatography or static light scattering.

As to a method for obtaining the crosslinked cationic polymer compound (B), the crosslinking structure can be introduced into the cationic polymer by conventional methods, such as a method which involves copolymerizing with other copolymerizable crosslinking agent to produce a crosslinked polymer when a corresponding cationic-group-including monomer is polymerized, and a method which involves crosslinking a cationic polymer with a crosslinking agent having two or more groups reactable with a functional group (for example, amino group) of the cationic polymer. When the functional group is an amino group, the following conventional compounds can be used: the compounds having two or more of such as epoxy groups, ketone groups, aldehyde groups, amide groups, halogenated alkyl groups, isocyanate groups, carboxyl groups, anhydride groups, acid halide groups, amide-bonding portions, ester-bonding portions, or active double bonds per a molecule. Examples of the above crosslinking agent include: bisepoxy compounds, epichlorohydrin, halohydrinsi, dihalides such as dibromoethylene, formalin, dialdehyde compounds such as glyoxal, diglycidyl ethers of (poly)ethylene glycols, diglycidyl ethers of (poly)propylene glycols, diglycidyl ethers of dialcohols such as neopentyl alcohol, polyglycidyl ethers of glycerol, methylenebisacrylamide, and diacrylate compounds, but the crosslinking agent is not limited thereto.

In addition, the cationic polymer compound (B) in the present invention favorably has a cation density of not less than 2 mmol/g, more favorably not less than 4 mmol/g, most favorably not less than 6 mmol/g. In the case where the cation density is less than 2 mmol/g, the shape-maintaining property or BBS of a water-absorbing agent aggregate after swelling might be insufficient in a water-absorbing agent obtained by a process including the step of blending the water-absorbent resin particles and the cationic polymer compound (B) together.

-Production Process for a Water-Absorbing Agent According to the Present Invention- The water-absorbing agent, according to the present invention, can be obtained by a process including the step of blending the water-absorbent resin particles (A) and the cationic polymer compound (B) together as obtained in the above way. Hereinafter, the production process for obtaining the water-absorbing agent according to the present invention is explained.

The production process for a water-absorbing agent according to the present invention can be carried out blending the water-absorbent resin particles (A) and the cationic polymer compound (B) together. When this blending is carried out, it is not always necessary to heat, and the water-absorbent resin particles (A) are blended with a solution (for example, aqueous solution) including the cationic polymer compound (B), or with a gel-like liquid or solid including the cationic polymer compound (B), or with a powdery cationic polymer compound (B).

Accordingly, the aimed water-absorbing agent is obtained. When the solution including the cationic polymer compound (B), or the gel-like liquid or solid including the cationic polymer compound (B) is used, an ion-bonding layer is formed on the surface of the water-absorbent resin particles (A) by the blending. When the powdery cationic polymer compound (B) is used, an ion-bonding layer is formed on the surface of the water-absorbent resin particles (A) by adding water while or after the blending. When the blending is carried out using water or a water-soluble organic solvent, such as aqueous solution, hydrophilic organic solvent solution, or gel-like liquid or solid, the drying may be carried out by heating after the blending if necessary. The drying is usually carried out at a temperature of favorably 30 to 170° C., more favorably 50 to 150° C.

In the present invention, various modes can be employed for blending the water-absorbent resin particles (A) and the cationic polymer compound (B). The blending is carried out by blending the water-absorbent resin particles (A) with a liquid drop of a solution (for example, aqueous solution) or a gel-like liquid including the cationic polymer compound (B), or by spraying each liquid to the water-absorbent resin particles (A) in order to blend them. When this blending is carried out, the following apparatuses can be utilized for example: high-speed-stirring blenders, gas-stream type blenders, moving-type blenders, and extruders. The blending can be carried out in the presence of such as organic powders (for example, cellulose powder) or inorganic powders (for example, silica fine particle). Furthermore, the water-absorbing agent as obtained may be dried if necessary.

In the present invention, the blending of the water-absorbent resin particles (A) and the cationic polymer compound (B) can be carried out in any stage such as: before the surface neighborhood of a water-absorbent resin is crosslinked with a special crosslinking agent; when a water-absorbent resin and a crosslinking agent is blended together; while the mixture of a water-absorbent resin and a crosslinking agent is heat-treated; after the mixture of a water-absorbent resin and a crosslinking agent is heat-treated to obtain the water-absorbent resin particles (A); after the mixture of a water-absorbent resin and a crosslinking agent is heat-treated and the resultant water-absorbent resin particles (A) are cooled; at a stage when the particle diameters of the water-absorbent resin particles (A) are adjusted to a specific range with a sieve; or before or after the stage. In addition, the blending may be carried out at two or more stages. Among the stages for the blending, the blending with the cationic polymer compound (B) is favorably carried out at the following stage: after the mixture of a water-absorbent resin and a crosslinking agent is heat-treated to obtain the water-absorbent resin particles (A) or after the mixture of a water-absorbent resin and a crosslinking agent is heat-treated and the resultant water-absorbent resin particles (A) are cooled. For example, an effective production process can be formed by blending with the cationic polymer compound (B) in a step of cooling the water-absorbent resin particles (A) as obtained by heat-treating the mixture of the water-absorbent resin and the crosslinking agent. In addition, the resultant water-absorbing agent can also be dried by utilizing residual heat at cooling.

In the present invention, the blending of the water-absorbent resin particles (A) and the cationic polymer compound (B) may be carried out under any temperature, but it is favorably carried out at 5 to 200° C., more favorably 25 to 130° C.

In the present invention, the respective temperatures of the water-absorbent resin particles (A) and the cationic polymer compound (B) when the water-absorbent resin particles (A) and the cationic polymer compound (B) are blended together are not especially limited, but they are favorably in the range of 5 to 200° C., more favorably 25 to 130° C. The respective temperatures of the water-absorbent resin particles (A) and the cationic polymer compound (B) may be different.

When the water-absorbent resin particles (A) and the cationic polymer compound (B) are blended together, and when the respective temperatures of the water-absorbent resin particles (A) and the cationic polymer compound (B) are different, the cooling effect may be obtained. For example, when the water-absorbent resin particles (A) of 60 to 200° C. and the cationic polymer compound (B) of 0 to 100° C. are blended together, the water-absorbing agent as obtained by the blending can effectively be cooled.

In the present invention, if necessary, the following materials can be added even in any stage such as before, while, or after the water-absorbent resin particles (A) and the cationic polymer compound (B) are blended together: organic powders such as cellulose powder, inorganic powders such as fine particulate silica, antioxidants and/or boric compounds, and surfactants. In addition, examples of the method for adding these materials include a method that involves directly adding them as they are, or a method that involves adding them in a form of aqueous solution. However, it is not especially limited. The amount of these as added is favorably not more than 5 weight %, more favorably not more than 1 weight % of the water-absorbent resin particles (A).

In addition, in the present invention, the water-absorbing agent may be obtained by blending the water-absorbent resin particles (A) and the cationic polymer compound (B) together and thereafter further blending the water-absorbent resin particles (A). The water-absorbent resin particles (A) as blended further may be or not be the same as of the water-absorbent resin particles (A) as blended in first time.

In addition, in the present invention, the water-absorbing agent may be obtained by blending the water-absorbent resin particles (A) having a specific particle range and the cationic polymer compound (B) together, and thereafter further blending the water-absorbent resin particles (A) having a specific particle range. In this production method, the following method is favorable for example: a method that involves the water-absorbent resin particles (A) having particle diameters of smaller than 300 μm and the cationic polymer compound (B) together, and thereafter further blending the water-absorbent resin particles (A) having particle diameters of not smaller than 300 μm. However, the method is not limited thereto.

In the present invention, immediately after the water-absorbent resin particles (A) and the cationic polymer compound (B) are blended together, the water-absorbing agent as obtained by the blending often has adhesion and difficult handling. This fact is especially remarkable when the water-absorbent resin particles (A) and an aqueous solution of the cationic polymer compound (B) are blended together. Therefore, the water-absorbing agent as obtained by the blending is favorably dried. The adhesion is decreased and the handling is improved because of the drying. The drying time of the water-absorbing agent in the present invention is usually in the range of 30 seconds to 60 minutes, favorably 1 to 30 minutes. In addition, the drying temperature is not especially limited, but it is favorably in the range of 30 to 170° C., more favorably 50 to 150° C.

In the present invention, the water-absorbent resin particles (A) are granulated by blending water-absorbent resin particles (A) and the cationic polymer compound (B) together, and the weight-average particle diameter of the water-absorbing agent as obtained in the above way can be enlarged larger than the average particle diameter of the water-absorbent resin particles (A). The weight-average particle diameter can be usually enlarged by 30 to 150 μm. In the same way, the ratio of the particles having particle diameters of not larger than 149 μm can be decreased to not more than 3 weight %. The powder is easily handled because of either or both of these, and the liquid permeability represented by such as SFC can also be improved.

In the present invention, the SFC of the water-absorbing agent as obtained can be increased more than that of the water-absorbent resin particles (A) by blending water-absorbent resin particles (A) and the cationic polymer compound (B) together.

In the present invention, the particle diameter of the water-absorbing agent is not especially limited, but it is favorable that the weight-average particle diameter in the range of 300 to 600 μm. It is more favorable that the water-absorbing agent favorably contains little fine particle (for example, not larger than 149 μm), for example, in an amount of not more than 5 weight %, more favorably not more than 3 weight %, particular favorably not more than 1 weight %.

If necessary, the following compounds can be added to the water-absorbing agent as obtained in the above way: organic powders such as cellulose powder, inorganic powders such as fine particulate silica, antioxidants and/or boric compounds, and surfactants. Particularly, the liquid permeability can be improved by adding inorganic powders such as fine particulate silica. The amount of these as added is favorably not more than 5 weight %, more favorably not more than 1 weight % of the water-absorbing agent.

In addition, a water-absorbing agent may be produced by blending two or more water-absorbing agents according to the present invention.

In addition, the cationic polymer compound (B) as blended can be isolated by stirring the present invention water-absorbing agent in a strong acidic aqueous solution such as hydrochloric acid. The cationic polymer compound (B) as isolated in the above away can be identified by conventional analyzing methods, such as nuclear magnetic resonance spectroscopy, infrared spectroscopy, or gel permeation chromatography.

When the water-absorbent resin particles (A) and the cationic polymer compound (B) are substantially ionically bonded in the water-absorbing agent according to the present invention, the following method is one method to make sure this. That is to say, when they are substantially ionically bonded, the water-absorbent resin particles (A) and the cationic polymer compound (B) cannot be separated very much even if the water-absorbing agent according to the present invention is stirred in pure water. However, the salt exchange is caused by stirring it in the strong acidic aqueous solution, and the ionic bond between the water-absorbent resin particles (A) and the cationic polymer compound (B) is dissociated, and these can nearly be isolated. These procedures are usually carried out by stirring in a liquid of which the weight is 200 times as much as the weight of the water-absorbing agent under room temperature (20 to 25° C.) in relative humidity of 40 to 60% at the liquid temperature of 20 to 25° C. The stirring time is one hour, and the stirring is mildly carried out, and hydrochloric acid of 0.1 N is used as the strong acidic aqueous solution. In the present invention water-absorbing agent, it is favorably that the water-absorbent resin particles (A) and the cationic polymer compound (B) are substantially ionically bonded. Therefore, when the water-absorbing agent according to the present invention is stirred in pure water by the above-mentioned method, the amount of the cationic polymer compound (B) as isolated is favorably not more than 50 weight %, more is favorably not more than 20 weight % of the cationic polymer compound (B) as included in the water-absorbing agent. When the water-absorbing agent according to the present invention is stirred in the strong acidic aqueous solution by the above-mentioned method, the amount of the cationic polymer compound (B) as isolated is favorably not less than 50 weight %, more is favorably not less than 80 weight % of the cationic polymer compound (B) as included in the water-absorbing agent.

The present invention water-absorbing agent as obtained by the above production process is, for example, obtained by blending 100 parts by weight of water-absorbent resin particles (A) and 0.01 to 10 parts by weight of a cationic polymer compound (B) together, wherein the cationic polymer compound (B) is obtained by a process including the step of crosslinking a cationic polymer with a crosslinking agent of which the amount is 0.01 to 10 weight % of the cationic polymer, and wherein the cationic polymer compound (B) has a water solubility of 70 to 10 weight % if the cationic polymer compound (B) is obtained from an ethylenimine monomer, otherwise the cationic polymer compound (B) has a water solubility of 100 to 10 weight %.

In addition, the present invention water-absorbing agent as obtained by the above production process is, for example, obtained by blending 100 parts by weight of water-absorbent resin particles (A) and 0.01 to 10 parts by weight of a cationic polymer compound (B) together, wherein the water-absorbent resin particles (A) exhibit an absorption capacity of not less than 20 g/g under a load of 4.9 kPa (AAP) and a gel layer liquid permeation rate of not more than 800 seconds under a load (FRUP), and wherein the cationic polymer compound (B) has a water solubility of 100 to 10 weight %.

In addition, the present invention water-absorbing agent as obtained by the above production process is, for example, obtained by blending 100 parts by weight of water-absorbent resin particles (A) and 0.01 to 10 parts by weight of a cationic polymer compound (B) together, wherein the water-absorbent resin particles (A) exhibit an absorption capacity of not less than 20 g/g under a load of 4.9 kPa (AAP) and a saline flow conductivity of not less than 20 ($10^{-7} \times cm^3 \times s \times g^{-1}$) (SFC), and wherein the cationic polymer compound (B) has a water solubility of 100 to 10 weight %.

In addition, these present invention water-absorbing agents as obtained by the above production processes favorably have the following values of 0.5 hrPT, 16 hrPT, $\Delta$PT, BBS, 16 hrBBS, DBBS, GV, AAP, and SFC.

In addition, the water-absorbing agent according to the present invention is also a water-absorbing agent having absorption properties as mentioned below.

-Absorption Properties of a Water-Absorbing Agent According to the Present Invention- The water-absorbing agent according to the present invention, which is obtained in the above way, is a novel water-absorbing agent having excellent absorption properties in comparison with conventional ones.

That is to say, the water-absorbing agent according to the present invention favorably exhibits a 16 hrPT and/or 0.5 hrPT of not more than 12.5 cm, more favorably not more than 11.0 cm, still more favorably not more than 9.0 cm. In the case where the 16 hrPT and/or 0.5 hrPT is not more than 12.5 cm, the water-absorbing agent aggregate has more excellent shape-maintaining property after it is swollen. In addition, in the case where the 16 hrPT is not more than 12.5 cm, the effect is maintained for a further long time after water is absorbed. In addition, when the water-absorbing agent is used as a portion of a water-absorbent structure such as disposable diapers (In general, the width of the water-absorbent structure is mostly in the range of 11 to 13 cm.) and when the 16 hrPT and/or 0.5 hrPT is not more than 12.5 cm, the properties of the water-absorbent structure is remarkably improved because the swollen water-absorbing agent in the water-absorbent structure is neither crushed nor one-sided by pressure such as body weight.

The water-absorbing agent according to the present invention favorably exhibits a $\Delta$PT of not more than 3.5 cm, more favorably not more than 2.0 cm. The value of the $\Delta$PT is calculated according to the following calculation equation. In the case where the $\Delta$PT is more than 3.5 cm, the shape-maintaining property deterioration of the water-absorbing agent aggregate after it is swollen with the passage of time is too increased. Therefore, when the water-absorbing agent is used for such as a water-absorbent structure for a long time, the properties thereof may be decreased extremely. In the case where $\Delta$PT is not more than 3.5 cm, the shape-maintaining property can be maintained sufficiently for a long time. When the water-absorbing agent is used for such as a water-absorbent structure, the properties of the water-absorbent structure are remarkably improved.

The water-absorbing agent according to the present invention favorably exhibits a BBS and/or 16 hrBBS of not less than 80 gf, more favorably not less than 95 gf. These values represent burst strength of gel layer as formed by the water-absorbing agent after it is swollen. In the case where the BBS and/or 16 hrBBS is less than 80 gf, the strength of gel layer is decreased rapidly. Therefore, the properties of the water-absorbent structure may be decreased extremely because the swollen water-absorbing agent in the water-absorbent structure cannot keep its shape sufficiently and the water-absorbent structure may be divided. In the case where the BBS and/or 16 hrBBS is not less than 80 gf, the water-absorbing agent can usually obtain sufficient burst strength of gel layer, and when it is used for such as a water-absorbent structure, the properties of the water-absorbent structure are remarkably improved. In addition, in the case where the 16 hrBBS is not less than 80 gf in particular, the sufficient burst strength of gel layer can be maintained for a long time.

The water-absorbing agent according to the present invention favorably exhibits a DBBS of not more than 40%, more favorably not more than 25%, still more favorably not more than 10%. In the case where the DBBS is more than 40%, the deterioration of burst strength of gel layer formed by the water-absorbing agent after it is swollen is too large with the passage of time. Therefore, when it is used for such as a water-absorbent structure for a long time, the properties thereof may be decreased extremely. In the case where the DBBS is not more than 40%, the sufficient burst strength of gel layer can usually be maintained for a long time. When the water-absorbing agent is used for such as a water-absorbent structure, the properties of the water-absorbent structure are remarkably improved.

In order to obtain more excellent water-absorbent structures, the GV of the water-absorbing agent is favorably not less than 23 g/g, more favorably not less than 25 g/g, still more favorably not less than 28 g/g, yet still more favorably not less than 31 g/g, most favorably not less than 35 g/g. This is for ensuring the absorption amount of water of the water-absorbent structure.

In addition, the AAP of the water-absorbing agent is favorably not less than 20 g/g, more favorably not less than 21.5 g/g, still more favorably not less than 23 g/g, yet still more favorably not less than 24.5 g/g, most favorably not less than 26 g/g in order to more extremely decrease a phenomenon such that the urine as absorbed in the water-absorbent structure is returned to the surface of the disposable diaper when the pressure is exerted to the water-absorbent structure by body weight.

The SFC of the water-absorbing agent according to the present invention is favorably not less than 25 ($10^{-7} \times cm^3 \times s \times g^{-1}$), more favorably not less than 35 ($10^{-7} \times cm^3 \times s \times g^{-1}$), still more favorably not less than 50 ($10^{-7} \times cm^3 \times s \times g^{-1}$) most favorably not less than 100 ($10^{-7} \times cm^3 \times s \times g^{-1}$). When the SFC is adjusted to not less than 25 ($10^{-7} \times cm^3 \times s \times g^{-1}$), the following effects are remarkably improved: when the water-absorbing agent according to the present invention is partially used as a water-absorbent structure of disposable diapers, the liquid permeability is improved, and the liquid spreads enough in the water-absorbent structure, and the absorption amount of water is increased, and the leak of the liquid is prevented.

In addition, the shape of the water-absorbing agent according to the present invention is widely selected from shapes such as sheet, gel, or fiber, but the shape is favorably a particulate shape. The water-absorbing agent exhibits the similar average particle diameter, particle size, water solubility, and water content as of the above water-absorbent resin.

In addition, as is shown in the above way, it is favorable that: the water-absorbent resin particles (A) and the cationic polymer compound (B) are substantially ionically bonded, or the ionic bond is substantially formed when they absorb water.

As is shown in the above way, the water-absorbing agent according to the present invention 1. favorably exhibits a GV of not less than 23 g/g, and an AAP of not less than 20 g/g, and a 16 hrPT of not more than 12.5 cm.

2. favorably exhibits a GV of not less than 23 g/g, and an AAP of not less than 20 g/g, and a 16 hrBBS of not less than 80 gf.

3. favorably exhibits a GV of not less than 23 g/g, and a 16 hrPT of not more than 12.5 cm, and a $\Delta$PT of not more than 3.5 cm.

4. favorably exhibits a GV of not less than 23 g/g, and a 0.5 hrPT of not more than 12.5 cm, and a $\Delta$PT of not more than 3.5 cm.

5. favorably exhibits a GV of not less than 23 g/g, and a 16 hrBBS of not less than 80 gf, and a $\Delta$PT of not more than 3.5 cm.

6. favorably exhibits a GV of not less than 23 g/g, and a BBS of not less than 80 gf, and a $\Delta$PT of not more than 3.5 cm.

7. favorably exhibits a GV of not less than 23 g/g, and a 16 hrPT of not more than 12.5 cm, and a DBBS of not more than 40%.

8. favorably exhibits a GV of not less than 23 g/g, and a 0.5 hrPT of not more than 12.5 cm, and a DBBS of not more than 40%.

9. favorably exhibits a GV of not less than 23 g/g, and a 16 hrBBS of not less than 80 gf, and a DBBS of not more than 40%.

10. favorably exhibits a GV of not less than 23 g/g, and a BBS of not less than 80 gf, and a DBBS of not more than 40%.

11. favorably exhibits a GV of not less than 23 g/g, and a SFC of not less than 50 ($10^{-7} \times cm^3 \times s \times g^{-1}$), and a 16 hrBBS of not less than 80 gf.

12. favorably exhibits a GV of not less than 23 g/g, and a SFC of not less than 50 ($10^{-7} \times cm^3 \times s \times g^{-1}$), and a BBS of not less than 80 gf.

13. favorably exhibits a GV of not less than 23 g/g, and a SFC of not less than 50 ($10^{-7} \times cm^3 \times s \times g^{-1}$), and a 16 hrPT of not more than 12.5 cm.

14. favorably exhibits a GV of not less than 23 µg, and a SFC of not less than 50 ($10^{-7} \times cm^3 \times s \times g^{-1}$), and a 0.5 hrPT of not more than 12.5 cm.

15. favorably exhibits a GV of not less than 23 g/g, and an AAP of not less than 20 g/g, and a 16 hrPT of not more than 12.5 cm or 16 hrBBS of not less than 80 gf.

16. favorably exhibits a GV of not less than 23 g/g, and a 16 hrPT or 0.5 hrPT of not more than 12.5 cm, and a $\Delta$PT of not more than 3.5 cm.

17. favorably exhibits a GV of not less than 23 g/g, and a 16 hrBBS or BBS of not less than 80 gf, and a $\Delta$PT of not more than 3.5 cm.

18. favorably exhibits a GV of not less than 23 g/g, and a 16 hrPT or 0.5 hrPT of not more than 12.5 cm or a 16 hrBBS or BBS of not less than 80 gf, and a $\Delta$PT of not more than 3.5 cm.

19. favorably exhibits a GV of not less than 23 g/g, and a DBBS of not more than 40%, and a 16 hrPT or 0.5 hrPT of not more than 12.5 cm.

20. favorably exhibits a GV of not less than 23 g/g, and a DBBS of not more than 40%, and a 16 hrBBS or BBS of not less than 80 gf.

21. favorably exhibits a GV of not less than 23 g/g, and a DBBS of not more than 40%, and a 16 hrPT or 0.5 hrPT of not more than 12.5 cm or a 16 hrBBS or BBS of not less than 80 gf.

22. favorably exhibits a GV of not less than 23 g/g, and a SFC of not less than 50 ($10^{-7} \times cm^3 \times s \times g^{-1}$), and a 16 hrPT or 0.5 hrPT of not more than 12.5 cm.

23. favorably exhibits a GV of not less than 23 g/g, and a SFC of not less than 50 ($10^{-7} \times cm^3 \times s \times g^{-1}$), and a 16 hrBBS or BBS of not less than 80 gf.

24. favorably exhibits a GV of not less than 23 g/g, and a SFC of not less than 50 ($10^{-7} \times cm^3 \times s \times g^{-1}$), and a 16 hrPT or 0.5 hrPT of not more than 12.5 cm or a 16 hrBBS or BBS of not less than 80 gf.

25. favorably comprises water-absorbent resin particles (A) and a cationic polymer compound (B), wherein the cationic polymer compound (B) is substantially ionically bonded to the water-absorbent resin particles (A), and wherein the water-absorbing agent exhibits a GV of not less than 23 g/g, an AAP of not less than 20 g/g, and a SFC of not less than 50 ($10^{-7} \times cm^3 \times s \times g^{-1}$).

The water-absorbing agents as recited in the above 3 to 24 more favorably exhibit an AAP of not less than 20 g/g, still more favorably the AAP as shown above.

The water-absorbing agents as recited in the above 1, 2, 3, 4, 5, 6, 7, 8, 9, 10, 15, 16, 17, 18, 19, 20, and 21 more favorably exhibit a SFC of not less than 25 ($10^{-7} \times cm^3 \times s \times g^{-1}$), still more favorably the SFC as shown above.

The water-absorbing agents as recited in the above 2, 4, 5, 6, 8, 9, 10, 11, 12, 14, 17, 20, 23, and 25 more favorably exhibit a 16 hrPT of not more than 12.5 cm, still more favorably the 16 hrPT as shown above.

The water-absorbing agents as recited in the above 1, 2, 3, 5, 6, 7, 9, 10, 11, 12, 13, 15, 17, 20, 23, and 25 more favorably exhibit a 0.5 hrPT of not more than 12.5 cm, still more favorably the 0.5 hrPT as shown above.

The water-absorbing agents as recited in the above 1, 2, 7, 8, 9, 10, 11, 12, 13, 14, 15, 19, 20, 21, 22, 23, 24, and 25 more favorably exhibit a ΔPT of not more than 3.5 cm, still more favorably the ΔPT as shown above.

The water-absorbing agents as recited in the above 1, 3, 4, 6, 7, 8, 10, 12, 13, 14, 16, 19, 22; and 25 more favorably exhibit a 16 hrBBS of not less than 80 gf, still more favorably the 16 hrBBS as shown above.

The water-absorbing agents as recited in the above 1, 2, 3, 4, 5, 7, 8, 9, 11, 12, 13, 14, 15, 16, 19, 22, 23, 24, and 25 more favorably exhibit a BBS of not less than 80 gf, still more favorably the BBS as shown above.

The water-absorbing agents as recited in the above 1, 2, 3, 4, 5, 6, 7, 11, 12, 13, 14, 15, 16, 17, 22, 23, 24, and 25 more favorably exhibit a DBBS of not less than 80 gf, still more favorably the DBBS as shown above.

The water-absorbing agents as recited in the above 1 to 24 more favorably comprises water-absorbent resin particles (A) and a cationic polymer compound (B), wherein the cationic polymer compound (B) is substantially ionically bonded to the water-absorbent resin particles (A).

These more favorable ranges of the AAP, SFC, 16 hrPT, 0.5 hrPT, ΔPT, BBS, 16 hrBBS, and DBBS as shown above are applied to the respective water-absorbing agents either alone respectively, still more favorably in combinations with each other.

Among the above water-absorbing agents, the water-absorbing agents as recited in the 1, 2, 4, 10, 12, 14, 16, 17, 18, 19, 20, 21, 22, 23, 24, and 25 are still more favorable, and the water-absorbing agents as recited in the 1, 2, 4, 10, and 25 are yet still more favorable.

For example, the water-absorbing agent as recited in the above 1 has a sufficient GV and an excellent AAP, and the shape-maintaining property of its swollen water-absorbing agent aggregate is maintained after water is absorbed even if long time passes. Therefore, when it is used for a water-absorbent structure, the remarkable improvement of the properties is caused.

In addition, for example, the water-absorbing agent as recited in the above 2 has a sufficient GV and an excellent AAP, and its BBS is maintained after water is absorbed even if long time passes. Therefore, when it is used for a water-absorbent structure, the remarkable improvement of the properties is caused.

In addition, for example, the water-absorbing agent as recited in the above 4 has a sufficient GV, and the shape-maintaining property of its swollen water-absorbing agent aggregate is excellent after water is absorbed, and the shape-maintaining property of its swollen water-absorbing agent aggregate is not worse with the passage of time. Therefore, when it is used for a water-absorbent structure, the remarkable improvement of the properties is caused.

In addition, for example, the water-absorbing agent as recited in the above 10 has a sufficient GV and an excellent BBS after water is absorbed, and the BBS is not worse with the passage of time. Therefore, when it is used for a water-absorbent structure, the remarkable improvement of the properties is caused.

In addition, for example, the water-absorbing agent as recited in the above 25 comprises the water-absorbent resin particles (A) and the cationic polymer compound (B), and has an especially excellent SFC, a sufficient GV, and an excellent AAP among water-absorbing agents in which the cationic polymer compound (B) is substantially ionically bonded to the water-absorbent resin particles (A). Therefore, when it is used for a water-absorbent structure, the remarkable improvement of the properties is caused.

In this way, for example, the water-absorbing agents as recited in the above 1 to 25 are novel water-absorbing agents exhibiting excellent absorption properties that are not conventionally found.

For example, these can be produced by the above production process of a water-absorbing agent. In addition, the shape thereof may be sheet, gel, or fiber, and it is not especially limited. However, the shape is favorably a particulate shape having the particle diameter range as shown above.

The water-absorbing agent according to the present invention has excellent absorption properties when it is used for a water-absorbent structure. That is to say, when the pressure is exerted to the water-absorbent structure by body weight, the following phenomenon is remarkably improved: the urine as absorbed in the water-absorbent structure is returned to the surface of the disposable diaper. In addition, when the water-absorbing agent according to the present invention is solely used as a water-absorbent structure or combined with materials such as cellulose fibers, it is difficult to cause the movement or dropping of the water-absorbing agent. Therefore, the effect is maintained for a long time after water is absorbed. In addition, the water-absorbing agent also has an excellent shape-maintaining property or BBS of a water-absorbing agent aggregate after it is swollen, and this effect is maintained for a long time. Because this shape-maintaining property or BBS of the water-absorbing agent aggregate after swelling is excellent, it is difficult to cause the movement of the swollen water-absorbing agent in the water-absorbent structure in practical use and the properties of the water-absorbent structure can be displayed sufficiently when the water-absorbing agent is used as a portion of the water-absorbent structure.

-Production Process for a Water-Absorbent Structure According to the Present Invention and its Absorption Properties- The water-absorbing agent as obtained by the above production process, for example, can be converted to a water-absorbent structure by combining with suitable materials, wherein the water-absorbent structure is fitted as an absorption layer of sanitary materials. Hereinafter, the water-absorbent structure according to the present invention is explained.

The water-absorbent structure according to the present invention is a shaped composition comprising a water-absorbent resin or a water-absorbing agent, and other material, wherein the water-absorbent resin or water-absorbing agent absorbs blood, body fluid, and urine, and is used for disposable diapers, sanitary napkins, incontinent pads, and medical pads. Examples of the material as used include cellulose fibers. Examples of the cellulose fibers include: wood pulp fibers such as mechanical pulp, chemical pulp, semichemical pulp, digested pulp obtained from wood; and artificial cellulose fibers such as rayon and acetates. Preferred cellulose fibers are wood pulp fibers. These cellulose fibers may partially include synthetic fibers, such as polyamides and polyesters. When the water-absorbing agent according to the present invention is used as a portion of a water-absorbent structure, the weight of the water-absorbing agent in the water-absorbent structure is favorably not less than 30 weight %, more favorably not less than 50 weight %, still more favorably not less than 70 weight %. In the case where the weight of the water-absorbing agent in the water-absorbent structure is less than 30 weight %, the sufficient effect may not be obtained.

In order to obtain a water-absorbent structure from the water-absorbing agent and cellulose fiber wherein the water-absorbing agent is obtained in the above way, the following conventional means for obtaining the water-absorbent structure can fitly be selected for example: a method which involves scattering a water-absorbing agent on paper or mat comprising a cellulose fiber, and interposing them if necessary; and a method which involves uniformly blending a cellulose fiber and a water-absorbing agent. A method, which involves dry-blending a water-absorbing agent and a cellulose fiber, and thereafter compressing them, is favorable. This method enables to remarkably prevent the water-absorbing agent from falling from the cellulose fiber. The compression is favorably carried out under heating condition, and the temperature is, for example, in the range of 50 to 200° C. In addition, in order to obtain the water-absorbent structure, the methods described in JP-A-509591/1997 and JP-A-290000/1997 are also favorably used.

As to the water-absorbing agent as obtained by the production process according to the present invention, the water-absorbing agent falls little from a combined counter material such as cellulose fibers even after it absorbs water and is swollen, and the swollen water-absorbing agent aggregate has an excellent shape-maintaining property and BBS. Therefore, the water-absorbing agent can be used as a water-absorbing-holding agent for various uses because it has excellent absorption properties. Examples of this water-absorbing-holding agent are described in the following:

(1) Water-absorbing-holding agent for absorbent article

Disposal diapers, sanitary napkins, incontinent pads, medical pads, and so on (2) Water-holding agent for agricultural, horticultural fields Substitute agents for water-soluble starch, soil-improving agents, water-holding agents, agents for maintaining effects of agricultural chemicals, and so on (3) Water-holding agent for architecture Dewfall preventives for interior-wallpaper agents, cement additives, and so on (4) Other Release-controlling agents, coolness-holding agents, disposal hand warmers, dirty-soil-solidifying agents, freshness-keeping agents for food, ion-exchange column materials, dehydration agents for sludge or oil, drying agents, humidity-adjusting materials, and so on In addition, when the water-absorbent structure according to the present invention is used for sanitary materials such as disposal diapers, sanitary napkins, incontinent pads, and medical pads, they are favorably used with comprising (a) a liquid-permeable top sheet as arranged adjacent to a body of a wearing person, (b) a liquid-impermeable back sheet as arranged adjacent to clothes of the wearing person and far away from the body of the wearing person, and (c) a water-absorbent structure as arranged between the top sheet and the back sheet. The water-absorbent structure may comprise two or more layers, or may be used together with such as a pulp layer.

In more favorable composition, the water-absorbing agent in the water-absorbent structure favorably has a unit weight of 60 to 1,500 $g/m^2$, more favorably 100 to 1,000 $g/m^2$, still more favorably 150 to 500 $g/m^2$.

In addition, in the present invention, various functions can also be given to the water-absorbing agent according to the present invention by further adding thereto materials such as disinfectants, deodorants, antimicrobial agents, perfumes, various inorganic powders, foaming agents, pigments, dyes, hydrophilic short fibers, manure, oxidants, reductants, water, and salts.

(Effects and Advantages of the Invention):

According to the present invention, is obtained the effect of enabling to provide the production process for a water-absorbing agent, in which, when used as a water-absorbent structure, the following phenomenon is remarkably improved: the urine as absorbed in the water-absorbent structure is returned to the surface of a disposable diaper; and when the water-absorbing agent according to the present invention is solely used as a water-absorbent structure or used in combination with materials such as cellulose fibers, it is difficult to cause the movement and the dropping of the water-absorbing agent; and the effects maintain for a long time even after water is absorbed; and it is difficult to cause the movement of the water-absorbing agent after swelling in the water-absorbent structure when it is practically used; and the properties of the water-absorbent structure can be displayed sufficiently.

According to the present invention, is obtained the effect of enabling to provide the water-absorbing agent, in which, when used as a water-absorbent structure, the following phenomenon is remarkably improved: the urine as absorbed in the water-absorbent structure is returned to the surface of a disposable diaper; and when the water-absorbing agent according to the present invention is solely used as a water-absorbent structure or used in combination with materials such as cellulose fibers, it is difficult to cause the movement and the dropping of the water-absorbing agent; and the effects maintain for a long time even after water is absorbed; and it is difficult to cause the movement of the water-absorbing agent after swelling in the water-absorbent structure when it is practically used; and the properties of the water-absorbent structure can be displayed sufficiently.

DETAILED DESCRIPTION OF THE PREFERRED EMBODIMENTS

Hereinafter, the present invention is more specifically illustrated by the following examples and comparative examples. However, the present invention is not limited to these examples. The simple units "%" and "part(s)" denote "weight %" and "part(s) by weight", respectively. Incidentally, the various performances of the water-absorbent resin particles, the cationic polymer compound, and the water-absorbing agent (as obtained by blending the water-absorbent resin particles and the cationic polymer compound together) were measured by the following methods. Unless otherwise noted in the following measurement, the measurement is carried out under room temperature (20 to 25° C.) in relative humidity of 40 to 60%, and the temperature of apparatuses and liquids as used is adjusted in the range of 20 to 25° C.

(a) Free Swelling Capacity (GV)

To a bag (60 mm×60 mm) made by nonwoven fabric, 0.2 g of water-absorbing agent was uniformly added, and then immersed in a large excess (usually, 500 ml) of aqueous sodium chloride solution of 0.9 weight % (physiological saline). The bag was pulled up after 60 minutes, and the weight (W1 (g)) of the bag was measured after draining off for 3 minutes with a centrifugal separator having centrifugal force as described in the edana ABSORBENCY II 441.1–99. In addition, the same procedure is carried out without using the water-absorbing agent, and then the weight (W0 (g)) of the bag was measured. Then, the value obtained by subtracting W0 from W1 was divided by the weight (g) of the water-absorbing agent, and the free swelling capacity (GV) was calculated by subtracting the weight (1 g/g) of the initial water-absorbing agent from the resultant value.

(b) Absorption Capacity Under a Load of 4.9 kPa (AAP)

0.9 g of water-absorbing agent or water-absorbent resin particle is uniformly spread on a stainless wire net of 400 mesh (mesh size: 38 μm) as attached by fusion to the bottom of a plastic supporting cylinder of an inner diameter 60 mm, on which a piston and a load are further mounted in sequence, wherein the piston has an outer diameter only a little smaller than 60 mm and makes no gap with the wall face of the supporting cylinder, but is not hindered from moving up and down, and the total weight of the piston and the load are adjusted to uniformly apply a load of 50 g/cm² (4.9 kPa) to the water-absorbing agent or water-absorbent resin particle. Then, the weight (Wa) of the resultant set of measurement apparatus is measured. A glass filter of 90 mm is mounted inside a Petri dish having a diameter of 150 mm, and a 0.9 weight % aqueous sodium chloride solution (physiological saline) is added up to the same level as the surface of the glass filter, on which a filter paper having a diameter of 90 mm is then mounted such that its entire surface will be wetted, and the excessive liquid is removed. The above set of measurement apparatus is mounted on the above wet filter paper, thereby allowing the water-absorbing agent or water-absorbent resin particle to absorb the liquid under a load. After 1 hour, the set of measurement apparatus is lifted, and its weight (Wb) is measured again. The absorption capacity under a load of 4.9 kPa was determined by subtracting Wa from Wb and by dividing the resultant value by the weight (0.9 g) of the water-absorbing agent or water-absorbent resin particle. In the present invention, the absorption capacity under a load of 4.9 kPa is abbreviated to AAP.

(c) Water Solubility

In a beaker of 1,000 ml, 0.01 g of cationic polymer compound is weighed out, and then 500 ml of hydrochloric acid of 0.1 mol/l is added thereto. After they are stirred for an hour, the resultant mixed solution is filtered with filter paper, and 20 ml of the filtrate is added to a beaker of 50 ml. A few drops of aqueous Toluidine Blue indicator solution (produced by Wako Pure Chemicals Co., Ltd.) as an indicator are added to the beaker. Then, a standard potassium polyvinyl sulfate solution of 1/400 (mol/l) (produced by Wako Pure Chemicals Co., Ltd.) is slowly dropped, when the point at which the color of the solution has changed from blue to reddish violet is regarded as the end point. When the theoretical amine value of the cationic polymer compound, the weight of the cationic polymer compound as eluted, and the titration amount of the standard potassium polyvinyl sulfate solution until the end point are regarded as Nc (eq/g), Wc (g), and V (ml), respectively, Wc is calculated from the following equation:

$$Wc(g) = (1/Nc) \times (1/400) \times V \times 500/(20 \times 1000)$$

The water solubility (weight %) is calculated from the following equation:

$$\text{Water solubility (weight \%)} = Wc/0.01 \times 100$$

(d) Gel Deformation Under a Load (16 hr Pressure Test)

Figure 2:
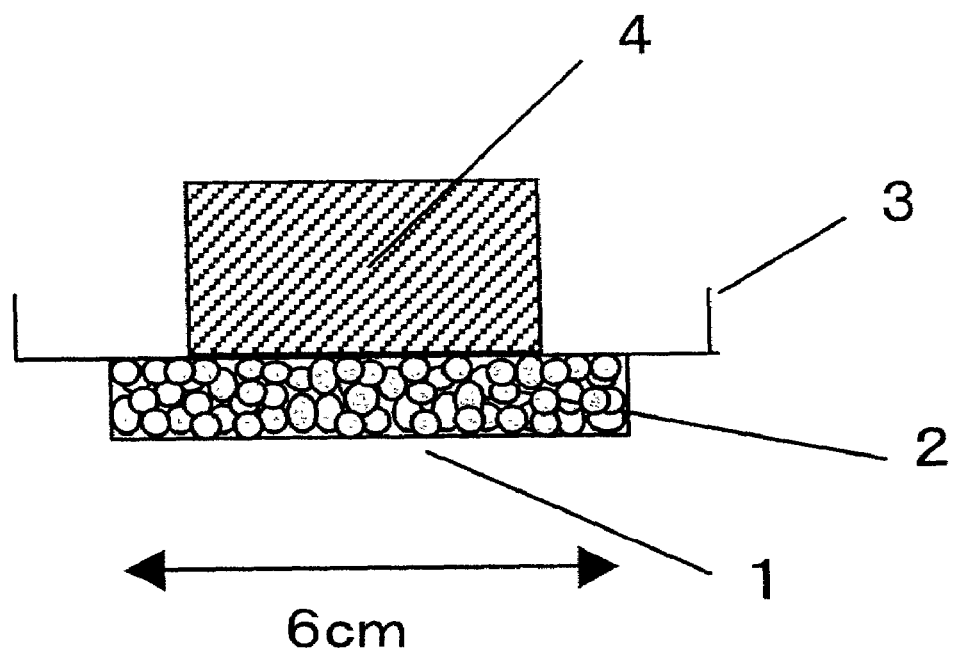
FIG. 2 is a schematic section of one measurement apparatus as used for measuring the gel deformation under a load (16 hrPT) or gel deformation under a short-time load (0.5 hrPT) which is one of the properties as displayed by the water-absorbing agent in the present invention, wherein the apparatus is used for forming swollen water-absorbing agent aggregates.

The procedure as described below is carried out in a room having room temperature (20 to 25° C.) and relative humidity of 40 to 60%. On a polypropylene round-dish-like (Petri-dish-like) receptacle 1 having a diameter of 6.0 cm and an edge height of 1.3 cm as described in FIG. 2, 1.5 g of water-absorbing agent is uniformly spread. Down to the receptacle, 30 g of aqueous sodium chloride solution of 0.9 weight % (physiological saline) is added for 30 seconds to swell the water-absorbing agent. Within 30 seconds after the physiological saline is added, a polypropylene round cover 3 having a diameter of 7.3 cm and a weight of 10.5 g is mounted in order to perfectly cover the round-dish-like receptacle 1 including the water-absorbing agent and the physiological saline, and 459 g of a weight 4 is further mounted thereon.

Figure 3:
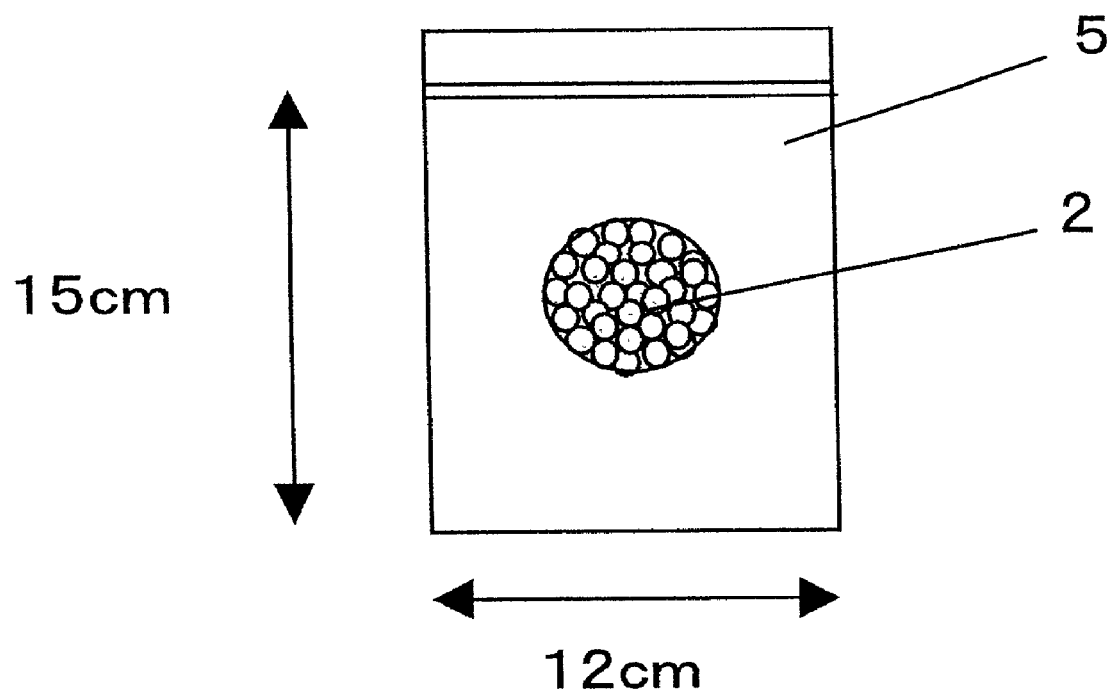
FIG. 3 is a schematic upper view of one measurement apparatus as used for measuring the gel deformation under a load (16 hrPT) or gel deformation under a short-time load (0.5 hrPT) which is one of the properties as displayed by the water-absorbing agent in the present invention, wherein the apparatus is used for storing swollen water-absorbing agent aggregates.

After being left still for 30 minutes under room temperature in this state, the receptacle is turned upside down, and the resultant swollen water-absorbing agent aggregate 2 (about 31.5 g of swollen gel aggregate) is taken out from the receptacle while the shape of the aggregate 2 in the receptacle is substantially kept. Next, as is described in FIG. 3, this swollen water-absorbing agent aggregate 2 (usually, columnar swollen gel aggregate having a diameter of about 6 to 8 cm and a height of about 1 to 1.5 cm) is added to a sealable plastic bag 5 having a size of: length 17 cm×width 12 cm×thickness 0.004 cm (Unipack F-4 produced by Seisan Nippon Co., Ltd.) so that the aggregate 2 can be arranged in the center of the bag while the shape of the aggregate 2 in the receptacle is substantially kept. Then, about 90% portion of the seal is closed, and the bag is left still under room temperature for 16 hours.

Figure 4:
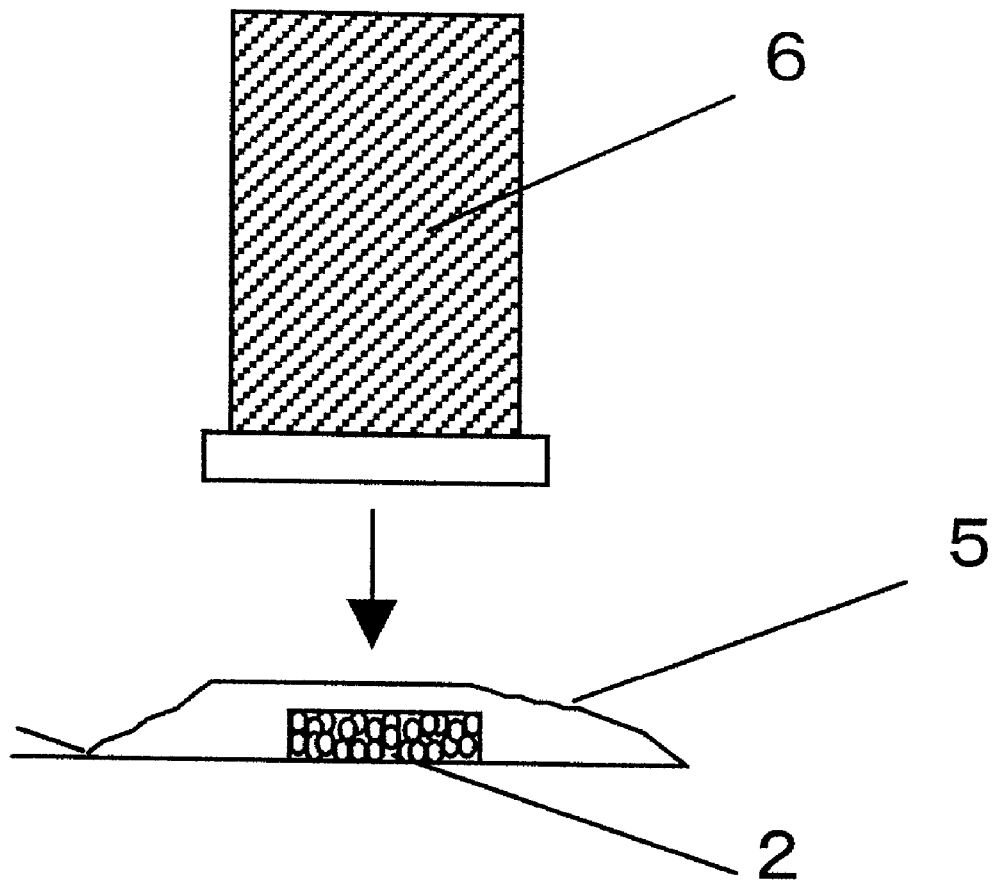
FIG. 4 is a schematic section of one measurement apparatus as used for measuring the gel deformation under a load (16 hrPT) or gel deformation under a short-time load (0.5 hrPT) which is one of the properties as displayed by the water-absorbing agent in the present invention, wherein the apparatus is used for pressurizing swollen water-absorbing agent aggregates.
Figure 5:
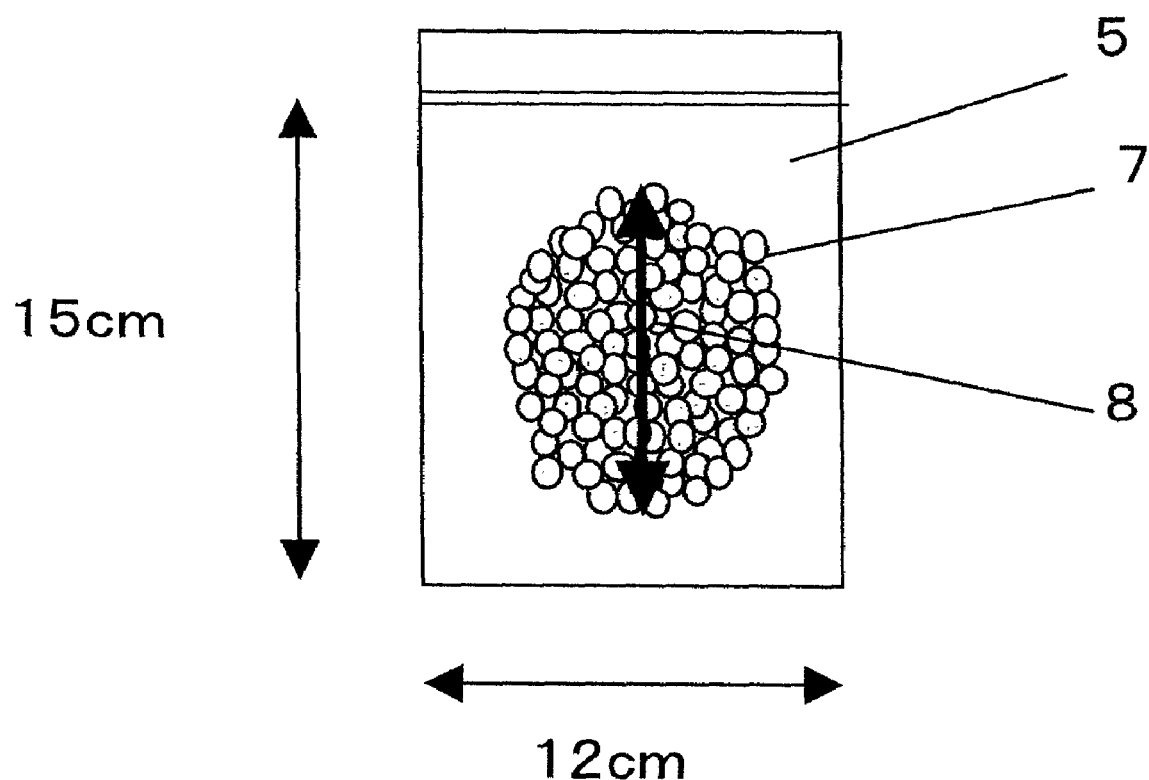
FIG. 5 is a schematic upper view of one image example when measuring the gel deformation under a load (16 hrPT) or gel deformation under a short-time load (0.5 hrPT) which is one of the properties as displayed by the water-absorbing agent in the present invention, wherein the one example shows deformed swollen water-absorbing agent aggregates as obtained after swollen water-absorbing agent aggregates are pressurized.

After the bag is left still, as is described in FIG. 4, a columnar weight 6 having a base area of 70.8 cm² and a weight of 3,485 g is mounted onto the plastic bag 5 including the swollen water-absorbing agent aggregate, so that the center of the swollen water-absorbing agent aggregate 2 can just overlap with the center of the columnar weight 6 when they are looked at from top. Then, they are pressurized by the weight of the weight 6 for one minute. The weight is removed after one minute, and the deformed gel resultant from the applied pressure is further left still for 30 seconds. After 30 seconds, as is described in FIG. 5, the straight distance 8 between two points, where the straight distance will be the longest from one arbitrary end to the other arbitrary end in the deformed swollen water-absorbing agent aggregate 7, is measured, and the resultant length is regarded as the gel deformation under a load (16 hr PT). The unit of the gel deformation under a load is expressed by cm. In addition, the gel deformation under a load is abbreviated to 16 hrPT.

(e) Gel Layer Liquid Permeation Rate Under a Load (FRUP)

A glass column equipped with a cock ("Biocolumn CF-30K", code of catalogue published by Iuchi Seiei Dou Co., Ltd.: 22-635-07, lower filter: #G2, inner diameter: 1 inch, and length: 400 mm) was packed with 0.5 g of water-absorbent resin particles, and the water-absorbent resin particles were equilibrium-swollen by an excess of physiological saline (for about 30 minutes to one hour). Next, as is shown in FIG. 1, after swollen water-absorbent resin particles A were sufficiently sedimented, a round plate C on which a weight B could be mounted and a pressurizing rod D under which a pressurizing plate I having a glass filter was arranged (The pressurizing plate I has the following size: thickness of 10 mm and diameter of 1 inch, and is equipped with the glass filter (#G0) in the lowest portion, and a disc thereon has a structure such that there are 84 bored holes having a diameter of 1 mm at regular intervals of 2 mm. The pressurizing plate I having the glass filter can freely be moved up and down in the glass column K, and has a structure such that the physiological saline can pass from the upper portion of the pressurizing plate I through the glass filter H.) are mounted on the swollen water-absorbent resin particles A while air is discharged. As is described in FIG. 1, the weight B was further mounted in order to uniformly apply a load of 24.5 g/cm$^2$ (2.4 kPa) to the swollen water-absorbent resin particles A. As is described in FIG. 1, the liquid surface was adjusted to a liquid height of 200 mm and the cock was opened, and then the time when the physiological saline J passed between two standard lines L (liquid surface having a liquid height of 150 mm) and M (liquid surface having a liquid height of 100 mm) as described in FIG. 1 (liquid amount: 25 ml according to measurement) was measured. Then, the average of the resultant three determinations was regarded as the gel layer liquid permeation rate (second) under a load (FRUP). Incidentally, when the present apparatus was used without the water-absorbent resin particles, the value as measured was 10 seconds. In the present invention, the gel layer liquid permeation rate under a load is abbreviated to FRUP.

(f) Average Particle Diameter and Particle Size

The particle distribution was obtained by classifying with JIS standard sieves (850 μm, 600 μm, 300 μm, 150 μm, and 45 μm), and was plotted on logarithmic probability paper to determine the weight-average particle diameter D50.

(g) Extractable Content

In 1,000 ml of deionized water, 0.5 g of water-absorbent resin or water-absorbent resin particles was dispersed, and they were stirred for 16 hours, and thereafter the resultant swollen gel was filtrated with filter paper. Then, the extractable content (weight %, relative to the water-absorbent resin particles) as eluted from the water-soluble polymer, namely the water-absorbent resin particles in the resultant filtrate was measured with colloidal titration, in which an aqueous Toluidine Blue indicator solution (produced by Wako Pure Chemicals Co., Ltd.) was used as an indicator, and a predetermined amount (usually 10 ml) of methylglycol chitosan solution of 0.005 mol/l (produced by Wako Pure Chemicals Co., Ltd.) was titrated with a standard potassium polyvinyl sulfate solution of 1/400 (mol/l) (produced by Wako Pure Chemicals Co., Ltd.).

(h) Water Content 1.0 g of water-absorbent resin or water-absorbent resin particles was placed on an aluminum cup, and it was dried in an airless dryer of 180° C. for 3 hours. Then, the water content was measured according to the weight decrease by the drying.

(i) Cation Density

In a beaker of 1,000 ml, 0.01 g of cationic polymer compound is weighed out, and then 500 ml of hydrochloric acid of 0.1 mol/l is added thereto. After they are stirred for 10 minutes, 20 ml of this solution was added to a beaker of 50 ml. To the beaker, a few drops of aqueous Toluidine Blue indicator solution (produced by Wako Pure Chemicals Co., Ltd.) as an indicator are added. Then, a standard potassium polyvinyl sulfate solution of 1/400 (mol/l) (produced by Wako Pure Chemicals Co., Ltd.) is slowly dropped, when the point at which the color of the solution has changed from blue to reddish violet is regarded as the end point. When the titration amount of the standard potassium polyvinyl sulfate solution until the end point is regarded as V (ml), the cation dencity is calculated from the following equation:

$$\text{Cation density (mmol/g)} = (V \times (1/400))/(0.01 \times (20/500))$$

(j) Saline Flow Conductivity (SFC) Test (Refer to JP-A-509591/1997)

The following test was carried out according to the saline flow conductivity (SFC) test as described in JP-A-509591/1997.

Figure 7:
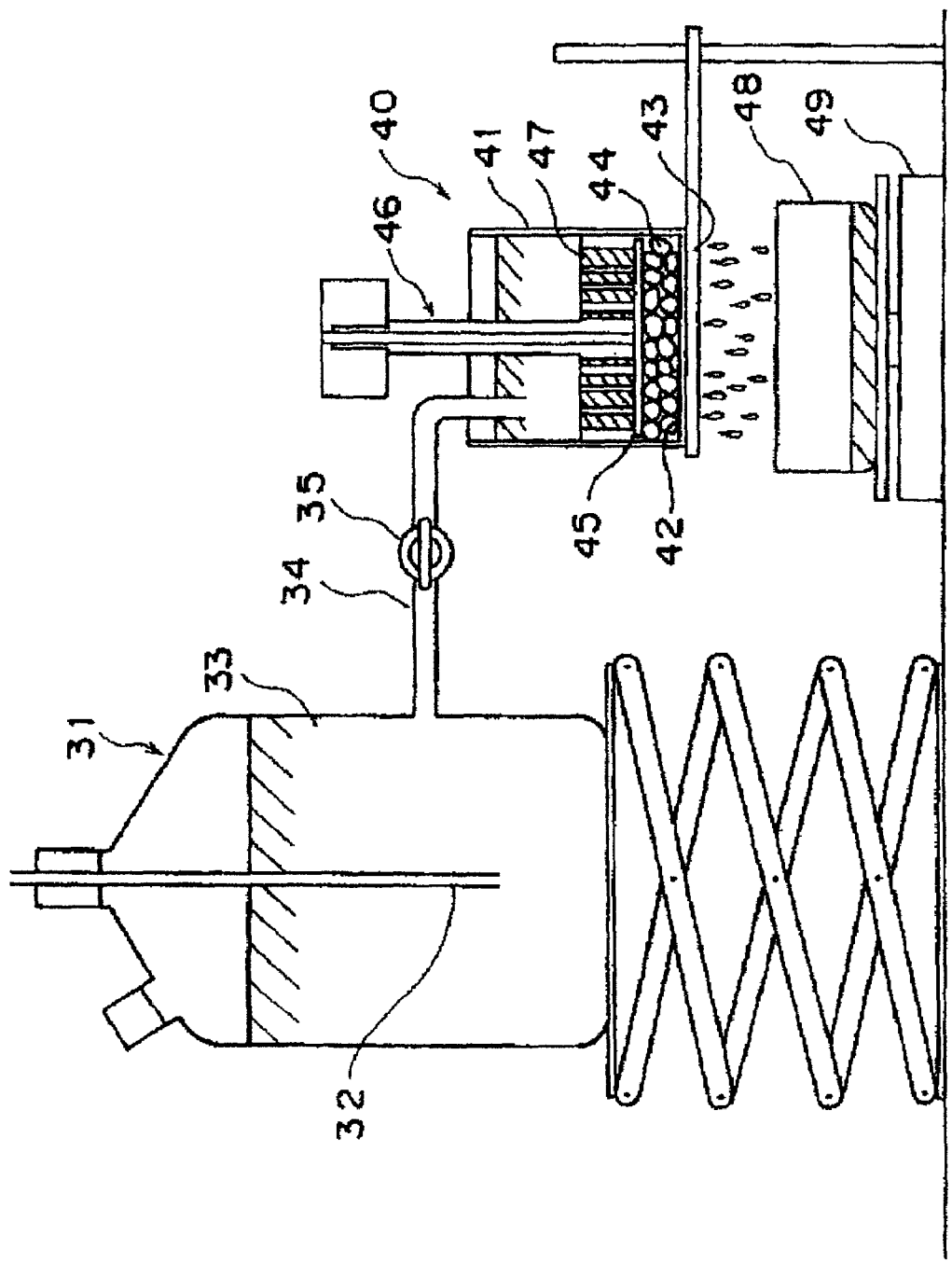
FIG. 7 is a schematic section of a measurement apparatus as used for measuring the saline flow conductivity (SFC).

An apparatus as described in FIG. 7 was used, and a water-absorbing agent (0.900 g) as uniformly added to a receptacle 40 was swollen in artificial urine for 60 minutes under a load of 0.3 psi (2.07 kPa), and the gel height of the resultant gel 44 was recorded. Next, under a load of 0.3 psi (2.07 kPa), an aqueous sodium chloride solution 33 of 0.69 weight % was passed through the swollen gel layer from a tank 31 under a constant hydrostatic pressure. This SFC test was carried out under room temperature (20 to 25° C.). The amount of the liquid passing through the gel layer versus time at twenty seconds' interval is recorded with a computer and a balance for 10 minutes. The flow rate through the swollen gel 44 (mainly among particles thereof), F$_s$(t) is determined in a unit of g/s by dividing the incremental weight (g) by incremental time (s). The time when the constant hydrostatic pressure and the stable flow rate are obtained is regarded as t$_s$, and only the data collected for times between t$_s$ and 10 minutes is used for flow rate calculations. F$_s$ (t=0) value, namely the initial flow rate through the gel layer is calculated from the flow rate between t$_s$ and 10 minutes. F$_s$ (t=0) is calculated by extrapolating the results of a least-squares fit of F$_s$ (t) versus time to t=0.

$$\text{Saline flow conductivity} = (F_s(t=0) \times L_0)/(\rho \times A \times \Delta P)$$

$$= (F_s(t=0) \times L_0)/139{,}506$$

where:
F$_s$ (t=0): flow rate in g/sec;
L$_0$: initial thickness of gel layer in cm;
ρ: density of NaCl solution (1.003 g/cm$^3$);

A: area of the upper side of gel layer in the cell 41 (28.27 cm$^2$);

ΔP: hydrostatic pressure applied to gel layer (4,920 dyne/cm$^2$); and the unit of the saline flow conductivity is: $10^{-7} \times cm^3 \times s \times g^{-1}$.

In the apparatus as described in FIG. 7, a glass tube 32 is inserted into the tank 31, and the lower end of the glass tube 32 was arranged so that the aqueous sodium chloride solution 33 of 0.69 weight % could be maintained in a height of 5 cm from the bottom of the swollen gel 44 in a cell 41. The aqueous sodium chloride solution 33 of 0.69 weight % in the tank 31 was supplied to the cell 41 through a L-tube 34 having a cock. A receptacle 48 to collect the passed liquid was arranged under the cell 41, and the collecting receptacle 48 was arranged on a balance 49. The inner diameter of the cell 41 was 6 cm, and a No. 400 stainless wire mesh 42 (mesh opening size of 38 μm) was arranged on the bottom thereof. Sufficient holes 47 where the liquid passed was arranged at the lower portion of a piston 46, and the bottom portion was equipped with a permeable glass filter 45 so that the water-absorbing agent or its swollen gel would not enter the holes 47. The cell 41 was placed on a stand to put on the cell. The face coming in contact with the cell was arranged on a stainless wire mesh 43 that did not inhibit liquid permeation.

The artificial urine (1) as used was obtained by adding: 0.25 g calcium chloride, dihydrate; 2.0 g of potassium chloride; 0.50 g of magnesium chloride hexahydrate; 2.0 g of sodium sulfate; 0.85 g of ammonium dihydrogen phosphate; 0.15 g of diammonium hydrogen phosphate; and 994.25 g of pure water.

(k) Ball Burst Strength (BBS) Test (Refer to JP-A-509591/1997)

The following test was carried out according to the ball burst strength (BBS) test as described in JP-A-509591/1997.

This test is for measuring the ball burst strength (BBS) of a water-absorbent agent at wet (swollen) state. The BBS of the water-absorbent agent is the force (peak load, in grams) required to rupture a water-absorbent agent gel layer that is swollen in the artificial urine (1) under procedures specified in this test method. The BBS of the water-absorbent agent is used for evaluation of the wet integrity of the water-absorbent agent that is swollen in the artificial urine (1).

(k-1) Sample Preparation Apparatus

Figure 8:
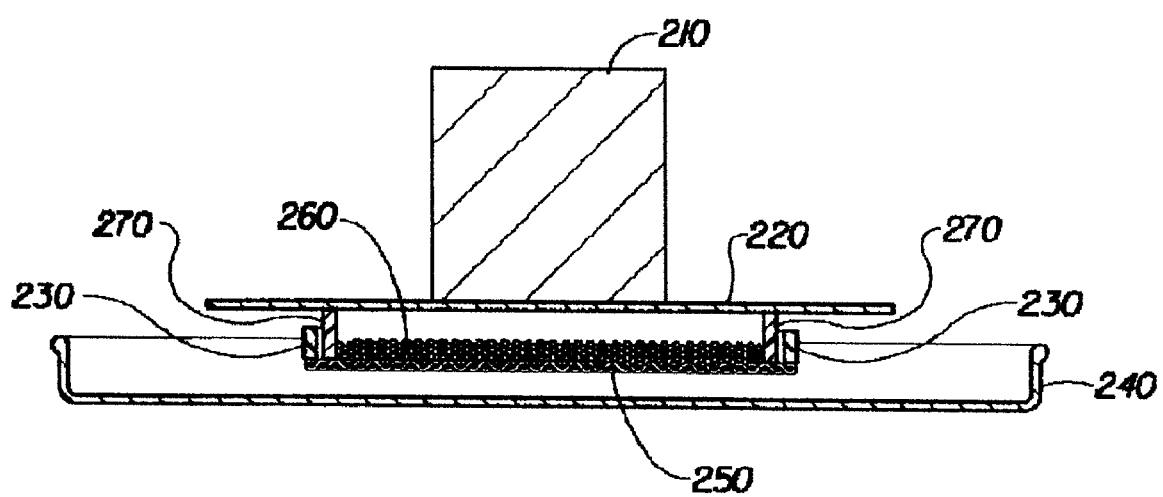
FIG. 8 is an illustrative view of a measurement apparatus as used for preparing a predetermined layer of swollen water-absorbing agents.

A suitable sample preparation apparatus for BBS measurement is described in FIG. 8. This apparatus comprises an inner-cylinder 270 that is used to contain a water-absorbent agent layer 260, a Teflon flat-bottomed tray 240, an inner-cylinder cover plate 220, and a stainless weight 210. The inner-cylinder 270 is bored from a transparent LEXAN rod (or its equivalent, for example, acryl resin rod) and has an inner diameter of 6.00 cm (=28.27 cm$^2$), a wall thickness of about 0.5 cm, and a height of about 1.50 cm. An outside-cylinder 230 is bored from a transparent LEXAN rod (or its equivalent, for example, acryl resin rod) and has an inner diameter slightly larger than the outside diameter of the inner-cylinder 270, so that the inner-cylinder 270 can exactly fit within the outside-cylinder 230 and slide freely. The outside-cylinder 230 has a wall thickness of about 0.5 cm, and a height of about 1.00 cm. The bottom of the outside-cylinder 230 is faced with a No. 400 mesh (mesh opening size of 38 μm) stainless-steel screen 250 that is biaxially stretched to tautness prior to attachment. The inner-cylinder cover plate 220 is made of glass plate with a thickness of 0.8 cm and a weight of 500 g. The stainless weight 210 has a weight of 1700 g.

(k-2) Burst Testing Machine

A tensile tester with a burst test load cell (Intelevt-II-STD Tensile Tester, Thwing Tester, produced by Thwing-Albert Instrument Co., Pennsylvania) is used for this test.

Figure 9:
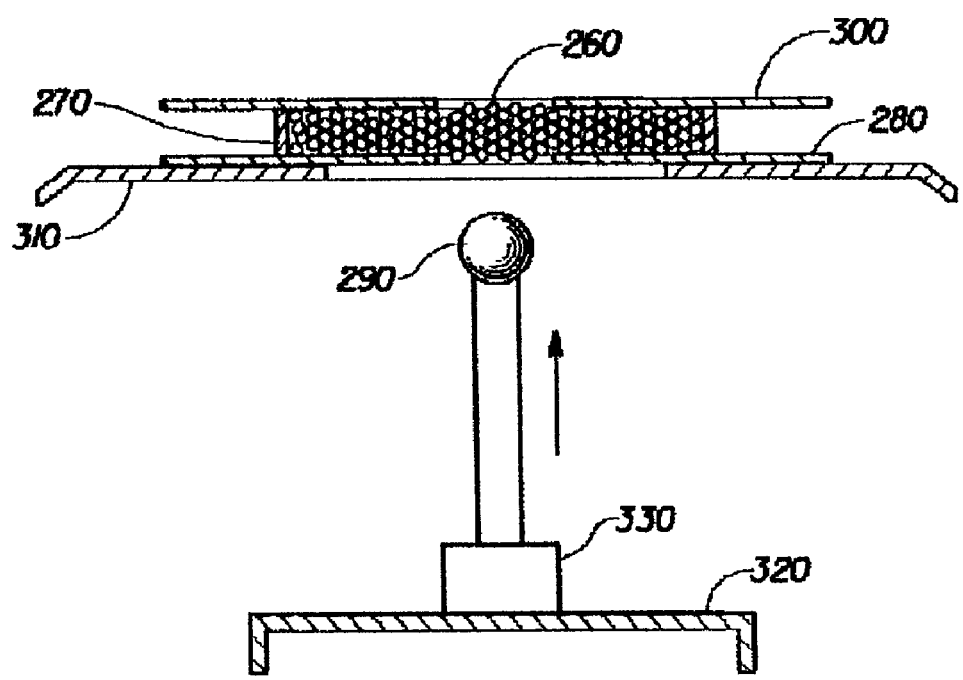
FIG. 9 is an illustrative view of a measurement apparatus as used for measuring a ball burst strength value (BBS) of water-absorbing agents.

As to FIG. 9, this apparatus comprises: a circular sample lower clamp platen 280 that is mount on a stationary crosshead 310 provided at the top of a dual screw instrument; a force sensing load cell 330 equipped with a polished stainless steel ball-shaped probe 290; a moving crosshead 320; and an upper clamping platen 300 that is used to clamp a sample 260 pneumatically. The lower clamp platen 280 is attached on the stationary crosshead 310. The force sensing load cell 330 is equipped with the probe 290. Both the lower clamp platen 280 and the upper clamp platen 300 have a diameter of 115 mm, a thickness of 2.9 mm, and a circular opening 18.65 mm in diameter. The polished stainless steel ball-shaped probe 290 has a diameter of 15.84 mm. The moving crosshead 320 moves up, and causes the probe 290 to contact and penetrate the sample 260. When the probe 290 penetrates the sample 260, it is considered that the test is completed, and the test result data are displayed and recorded.

(k-3) Procedure

As to FIG. 8, the inner-cylinder 270 was inserted into the outside-cylinder 230. To the inner-cylinder 270, 1.4 g aliquot of the water-absorbent agent was added and dispersed uniformly on the 400 mesh (mesh opening size of 38 μm) stainless screen 250 of the bottom by gently shaking and/or tapping of the assembled cylinders. The assembled cylinders including the water-absorbent agent were transferred to the Teflon flat-bottomed tray 240, and the inner-cylinder cover plate 220 was positioned onto the inner-cylinder 270. To the Teflon flat-bottomed tray, 240, 42.0 ml of the artificial urine (1) was added. The artificial urine (1) passed through the stainless screen 250 from the Teflon flat-bottomed tray 240. All of the artificial urine (1) as added was absorbed by the water-absorbent agent 260 within 5 minutes. Then, the stainless weight 210 was placed onto the inner-cylinder cover plate 220. After further 25 minutes, the stainless weight 210 and the inner-cylinder cover plate 220 were removed. Consequently, the predetermined layer 260 of the swollen water-absorbent agent for the BBS measurement has been prepared. The inner-cylinder 270 including the water-absorbent agent gel layer 260 was immediately transferred to the burst testing machine for the BBS test.

As to FIG. 9, the inner-cylinder 270 including the water-absorbent agent gel layer 260 was positioned on the lower clamp platen 280 and was fixed pneumatically with the upper clamping platen 300. With a break sensitivity of 10.00 g and a test speed of 5.00 inch/minutes, the test was initiated by pressing a test switch. The moving crosshead 320 moved up, and the polished stainless steel ball-shaped probe 290 penetrated the water-absorbent agent gel layer 260. After a sample burst was recorded, the moving crosshead 320 returned to a start position. The BBS is expressed as peak load grams. The average of three determinations should be reported. The unit of the BBS is expressed as gf. The ball burst strength is abbreviated to BBS.

(l) 16 Hours' Ball Burst Strength Test (16 hrBBS)

The same measurement method as of the above ball burst strength (BBS) test is carried out. In the above procedure (k-3), the stainless weight 210 and the inner-cylinder cover plate 220 were removed after 25 minutes from the end of the addition of the artificial urine (1), but the present measurement was carried out changing this 25 minutes to 16 hours. The 16 hours' ball burst strength is abbreviated to 16 hrBBS.

(m) Gel Deformation Under a Short-Time Load (0.5 hr Pressure Test)

The same measurement was carried out except that: still leaving for 16 hours under room temperature is changed to still leaving for 30 minutes under room temperature in the measurement method of the above (d) gel deformation under a load. The unit of the gel deformation under a short-time load is expressed as cm. In the present invention, the gel deformation under a short-time load is abbreviated to 0.5 hrPT.

(n) Gel Deformation Deterioration Under a Load with the Passage of Time (ΔPT)

The gel deformation deterioration under a load with the passage of time (ΔPT) is expressed by the following equation. This value means extent of gel deformation deterioration under a load with the passage of time.

Gel deformation deterioration under a load with the passage of time (ΔPT) = (gel deformation under a load) −

(gel deformation under a short-time load) = (16 hrPT) − (0.5 hrPT)

The gel deformation under a short-time load (0.5 hrPT) is measured by the above-mentioned method. The unit of the gel deformation deterioration under a load with the passage of time (ΔPT) is expressed as cm. In addition, the gel deformation deterioration under a load with the passage of time is abbreviated to ΔPT in the present invention. The ΔPT may be a negative value.

(o) Deterioration of Ball Burst Strength (DBBS)

The deterioration of ball burst strength is expressed by the following equation. This value means extent of deterioration of ball burst strength.

Deterioration of ball burst strength (DBBS) = 1 −

(16 hours' ball burst strength)/

[(ball burst strength)] × 100

= [1 − (16 hr BBS)/

(BBS)] × 100

The deterioration of ball burst strength is abbreviated to DBBS. The unit of the DBBS is expressed as %. The DBBS may be a negative value.

REFERENTIAL EXAMPLE 1

In a reactor as prepared by lidding a jacketed stainless twin-arm kneader of 10 liters in capacity with two sigma-type blades, a reaction liquid was obtained by dissolving 0.08 mol % of polyethylene glycol diacrylate (average molecular weight: 487) in 5,500 g of aqueous sodium acrylate solution having a neutralization ratio of 71.3 mol % (monomer concentration: 38 weight %). Next, this reaction liquid was degassed under an atmosphere of nitrogen for 30 minutes. Continuously, 2.9 g of ammonium persulfate and 0.08 g of L-ascorbic acid were added thereto while being stirred, and then the reaction was started after about one minute. Then, the polymerization was carried out at 20 to 90° C. while the resultant formed gel was pulverized, and a crosslinked hydrogel polymer (1) was taken out after 30 minutes from the start of the polymerization.

The crosslinked hydrogel polymer (1) as obtained was pulverized wherein its diameter was not larger than about 5 mm. This pulverized crosslinked hydrogel polymer (1) was spread on a metal gauze with 50 mesh (a mesh opening size of 300 μm), and hot-wind-dried at 180° C. for 50 minutes. Next, the resultant dry material was pulverized with a roll mill, and further classified with JIS vibration sieves having mesh opening sizes of 850 μm and 150 μm, thus obtaining an irregularly pulverized particulate water-absorbent resin (1) with an average particle diameter of 450 μm wherein the ratio of resins having particle diameters of not larger than 149 μm was 3%, a GV of 32 g/g, an uncrosslinked water-extractable content of 8 weight % in the water-absorbent resin, and a water content of 5 weight %.

A solution, which included a surface-crosslinking agent comprising 5 parts by weight of 1,4-butanediol, 2.5 parts by weight of isopropyl alcohol, and 15 parts by weight of water, was added to 500 parts by weight of the water-absorbent resin (1) while being stirred. The resultant mixture was added to a mortar mixer of 5 L, and stir-treated for 30 minutes while being heated in an oil bath of 212° C., thus obtaining water-absorbent resin particles (A-1) which exhibits a GV of 25.6 g/g, an AAP of 22.4 g/g, a FRUP of 70 seconds, and a SFC of 101 (unit: $10^{-7} \times cm^3 \times s \times g^{-1}$). The results were summarized in Table 1.

REFERENTIAL EXAMPLE 2

In a reactor as prepared by lidding a jacketed stainless twin-arm kneader of 10 liters in capacity with two sigma-type blades, a reaction liquid was obtained by dissolving 0.05 mol % of polyethylene glycol diacrylate (average molecular weight: 487) in 5,500 g of aqueous sodium acrylate solution having a neutralization ratio of 71.3 mol % (monomer concentration: 38 weight %). Next, this reaction liquid was degassed under an atmosphere of nitrogen for 30 minutes. Continuously, 2.9 g of ammonium persulfate and 0.08 g of L-ascorbic acid were added thereto while being stirred, and then the reaction was started after about one minute. Then, the polymerization was carried out at 20 to 90° C. while the resultant formed gel was pulverized, and a crosslinked hydrogel polymer (2) was taken out after 30 minutes from the start of the polymerization.

The crosslinked hydrogel polymer (2) as obtained was pulverized wherein its diameter was not larger than about 5 mm. This pulverized crosslinked hydrogel polymer (1) was spread on a metal gauze with 50 mesh (a mesh opening size of 300 μm), and hot-wind-dried at 180° C. for 50 minutes. Next, the resultant dry material was pulverized with a roll mill, and further classified with JIS vibration sieves having mesh opening sizes of 850 μm and 150 μm, thus obtaining an irregularly pulverized particulate water-absorbent resin (2) with an average particle diameter of 470 μm wherein the ratio of resins having particle diameters of not larger than 149 μm was 3%, a GV of 36 g/g, an uncrosslinked water-extractable content of 10 weight % in the water-absorbent resin, and a water content of 6 weight %.

A solution, which included a surface-crosslinking agent comprising 5 parts by weight of 1,4-butanediol, 2.5 parts by weight of isopropyl alcohol, and 15 parts by weight of water, was added to 500 parts by weight of the water-absorbent resin (2) while being stirred. The resultant mixture was added to a mortar mixer of 5 L, and stir-treated for 30 minutes while being heated in an oil bath of 212° C., thus obtaining water-absorbent resin particles (A-2) which exhibited a GV of 29.2 g/g, an AAP of 25.1 g/g, a FRUP of 220 seconds, and a SFC of 40 (unit: $10^{-7} \times cm^3 \times s \times g^{-1}$). The results were summarized in Table 1.

REFERENTIAL EXAMPLE 3

To 100 parts of 10% aqueous solution of polyallylamine (commercial name: PAA-10C, weight-average molecular weight: about 10,000, produced by Nitto Bouseki Co., Ltd.), 0.25 part of ethylene glycol diglycidyl ether (commercial name: Denacol EX810, produced by Nagase Kasei Kogyo Co., Ltd.) as a crosslinking agent was added while being stirred, and they were also stirred for one minute after they were blended. This was left still at 60° C. for one hour, thus obtaining an aqueous solution of a cationic polymer compound (B-1). The cationic polymer compound (B-1) had a water solubility of 97% and a cation density of 17 mmol/g.

REFERENTIAL EXAMPLE 4

To 100 parts of 10% aqueous solution of polyethylenimine (number-average molecular weight: about 70,000, produced by Nippon Shokubai Co., Ltd., cation density: 23 mmol/g), 0.5 part of ethylene glycol diglycidyl ether (commercial name: Denacol EX810, produced by Nagase Kasei Kogyo Co., Ltd.) as a crosslinking agent was added while being stirred, and they were also stirred for one minute after they were blended. This was left still at 60° C. for one hour, thus obtaining an aqueous solution of a cationic polymer compound (B-2). The cationic polymer compound (B-2) had a water solubility of 38. % and a cation density of 22 mmol/g.

REFERENTIAL EXAMPLE 5

To a beaker of 1,000 ml, 350 g of N-vinylformamide and 1,390 g of pure water were added, and this resultant reaction liquid was degassed under an atmosphere of nitrogen for 30 minutes. Continuously, 1.48 g of V-50 (Wako Pure Chemicals Co., Ltd.) was added to the reaction liquid while being stirred, and the resultant mixture was heated at 65° C. Then, the reaction was started after about one minute. The resultant polymer was sedimented in ethanol after 16 hours and thereafter dried, thus obtaining poly(N-vinylformamide).

The poly(N-vinylformamide) as obtained in the above way was converted to its aqueous solution of 5 weight %, and 0.5 equivalent of sodium hydroxide relative to the weight of the polymer was added thereto. Then, the reaction was carried out at 75° C. for 2 hours, thus obtaining an aqueous solution of a cationic polymer compound (B-3) that was a partially hydrolyzed poly(N-vinylformamide). The cationic polymer compound (B-3) had a water solubility of 99% and a cation density of 6 mmol/g.

In addition, the poly(N-vinylformamide) as obtained was converted to its aqueous solution of 5 weight %, and 1.5 equivalent of sodium hydroxide relative to the weight of the polymer was added thereto. Then, the reaction was carried out at 75° C. for 4 hours, thus obtaining an aqueous solution of polyvinylamine as hydrolyzed poly(N-vinylformamide).

REFERENTIAL EXAMPLE 6

To 100 parts of 10% aqueous solution of the polyvinylamine as obtained in Referential Example 5, 0.05 part of ethylene glycol diglycidyl ether (commercial name: Denacol EX810, produced by Nagase Kasei Kogyo Co., Ltd.) as a crosslinking agent was added while being stirred, and they were also stirred for one minute after they were blended. This was left still at 60° C. for one hour, thus obtaining an aqueous solution of a cationic polymer compound (B-4). The cationic polymer compound (B-4) had a water solubility of 97% and a cation density of 12 mmol/g.

COMPARATIVE REFERENTIAL EXAMPLE 1

Making reference to a production example of a water-absorbent resin and Example 1 as described in JP-A-31362/1993, its tracing test was carried out in the following procedure:

A crosslinked hydrogel polymer was obtained by polymerizing 4,000 parts of 37% aqueous solution of an acrylic salt monomer comprising 74.95 mol % of sodium acrylate, 25 mol % of acrylic acid, and 0.05 mol % of trimethylolpropane triacrylate with 2.0 parts of ammonium persulfate and 0.08 part of L-ascorbic acid under an atmosphere of nitrogen at 30 to 80° C. After the crosslinked hydrogel polymer as obtained was dried in a hot-wind-dryer of 150° C., and pulverized with a hammer mill, and classified with a metal gauze having 20 mesh (a mesh opening size of 850 μm, Tyler standard sieve), thus obtaining a 20-μm-passed material. This material is named a water-absorbent resin (3). To 100 parts of the water-absorbent resin (3), 0.5 part of glycerin, 2 parts of water, and 2 parts of ethyl alcohol were added and blended, and thereafter they were heat-treated at 210° C. for 10 minutes, thus obtaining water-absorbent resin particles (C-1) of which the surface neighborhood was secondarily crosslinked. The water-absorbent resin particles (C-1) exhibited a GV of 34.1 g/g, an AAP of 8.2 g/g, a FRUP of 2,000 seconds, and a SFC of 2 (unit: $10^{-7} \times cm^3 \times s \times g^{-1}$). The results were summarized in Table 1.

COMPARATIVE REFERENTIAL EXAMPLE 2

Making reference to Referential Example 4 as described in JP-A-95955/2000, its tracing test was carried out in the following procedure:

A stainless reactor of 20 L equipped with a dropping funnel, a stirrer, a thermometer, and a condenser was charged with 10 L of a cyclohexane solution including 100 g of inorganic particles (commercial name: Aerosil R972, produced by Nippon Aerosil Co., Ltd.), and they were stirred under room temperature. Next, to an aqueous polyethylenimine solution (as cooled at 0° C. beforehand) comprising 5,636 g of 30% polyethylenimine (commercial name: Epomin P-1000, produced by Nippon Sholubai Co., Ltd., cation density: 23 mmol/g) and 4,000 g of pure water, 363 g of 50% aqueous solution of ethylene glycol diglycidyl ether (commercial name: Denacol EX810, produced by Nagase Kasei Kogyo Co., Ltd.) as a crosslinking agent was added while being stirred, thus preparing an aqueous solution including the crosslinking agent and a hydrophilic polymer. Then, this solution was added to the cyclohexane solution under room temperature while being stirred. The system temperature was gradually raised to 65° C. while being stirred, and the reaction was carried out at 65° C. for 3 hours. Thereafter, the system temperature was cooled to room temperature, and the resultant formed spherical hydrogel was filtrated by aspiration, and the resultant spherical hydrogel was dried under reduced pressure at 60° C. for 48 hours, thus obtaining a fine water-swellable resin particle having a water content of 15% and a cationic group. This was named a cationic polymer compound (D-1). The cationic polymer compound (D-1) had a water solubility of 5%.

COMPARATIVE REFERENTIAL EXAMPLE 3

Making reference to Referential Example 2 as described in JP-A-3123/1997, its tracing test was carried out in the following procedure:

In 5,500 g of aqueous sodium acrylate solution having a neutralization ratio of 75 mol % (monomer concentration: 38 weight %), 7 g of trimethylolpropane triacrylate and 1 g of polyoxyethylene sorbitan monostearate were dissolved, and they were degassed under an atmosphere of nitrogen. Thereafter, 2.3 g of potassium persulfate and 0.11 g of L-ascorbic acid were added thereto to carry out polymerization. When the polymerization was finished, the crosslinked hydrogel polymer was further pulverized and dried in a hot-wind-dryer of 150° C. until the water content of the crosslinked hydrogel polymer was not more than 5%. The resultant dried product was pulverized with a roll granulator to collect a 20-mesh-passed material from a metal gauze. This material had an average particle diameter of about 390 µm, and the ratio of particles having particle diameters of smaller than 106 µm was 5 weight %. To 100 parts by weight of the 20-mesh-passed material, an aqueous liquid comprising 0.5 part of glycerin, 3 parts of water, and 0.75 part of isopropyl alcohol was added to blend them, and the resultant mixture was heat-treated at 200° C. for 33 minutes, thus obtaining water-absorbent resin particles (C-2) having a weak acidic group. The water-absorbent resin particles (C-2) exhibited a GV of 28.2 g/g, an AAP of 21.3 g/g, a FRUP of 1,214 seconds, and a SFC of 10 (unit: $10^{-7} \times cm^3 \times s \times g^{-1}$). The results were summarized in Table 1.

EXAMPLE 1

To 100 parts of the water-absorbent resin particles (A-1) as obtained in Referential Example 1, 10 parts of 10% aqueous solution of the cationic polymer compound (B-1) as obtained in Referential Example 3 was added to blend them, and they were heat-dried at 90° C. for 20 minutes. Thereafter, the resultant mixture was classified with a sieve having a mesh opening size of 850 µm, thus obtaining particles of not larger than 850 µm. These are named a water-absorbing agent (1). The various properties of the water-absorbing agent (1) as obtained are listed in Tables 2 and 3.

EXAMPLE 2

To 100 parts of the water-absorbent resin particles (A-1) as obtained in Referential Example 1, 15 parts of 10. % aqueous solution of the cationic polymer compound (B-2) as obtained in Referential Example 4 was added to blend them, and they were heat-dried at 90° C. for 20 minutes. Thereafter, the resultant mixture was classified with a sieve having a mesh opening size of 850 µm. These are named a water-absorbing agent (2). The various properties of the water-absorbing agent (2) as obtained are listed in Tables 2 and 3.

EXAMPLE 3

To 100 parts of the water-absorbent resin particles (A-2) as obtained in Referential Example 2, 5 parts of 10% aqueous solution of the cationic polymer compound (B-1) as obtained in Referential Example 3 was added to blend them, and they were heat-dried at 120° C. for 20 minutes. Thereafter, the resultant mixture was classified with a sieve having a mesh opening size of 850 µm, thus obtaining particles of not larger than 850 µm. These are named a water-absorbing agent (3). The various properties of the water-absorbing agent (3) as obtained are listed in Tables 2 and 3.

EXAMPLE 4

To 100 parts of the water-absorbent resin particles (A-1) as obtained in Referential Example 1, 3 parts of 50% aqueous solution of polyallylamine hydrochloride (PAA-HCl-3L, weight-average molecular weight: about 10,000, produced by Nitto Boseki Co., Ltd, and cation density: 11 mmol/g) was added to blend them, and they were heat-dried at 90° C. for 20 minutes. Thereafter, the resultant mixture was classified with a sieve having a mesh opening size of 850 µm, thus obtaining particles of not larger than 850 µm. These are named a water-absorbing agent (4). The various properties of the water-absorbing agent (4) as obtained are listed in Tables 2 and 3.

EXAMPLE 5

To 100 parts of the water-absorbent resin particles (A-2) as obtained in Referential Example 2, 20 parts of 30% aqueous solution of polyethylenimine (number average molecular weight: about 70,000, produced by Nippon Shokubai Co., Ltd., and cation density: 23 mmol/g) was added to blend them, and they were heat-dried at 120° C. for 30 minutes. Thereafter, the resultant mixture was classified with a sieve having a mesh opening size of 850 µm, thus obtaining particles of not larger than 850 µm. To these particles, 1 part of silicon oxide of super-fine particle (produced by Nippon Aerosil Co., Ltd., commercial name: Aerosil 200) was further added to blend them. This is named a water-absorbing agent (5). The various properties of the water-absorbing agent (5) as obtained are listed in Tables 2 and 3.

EXAMPLE 6

To 100 parts of the water-absorbent resin particles (A-1) as obtained in Referential Example 1, 15 parts of 5% aqueous solution of polyamidine (produced by HYMO Co., Ltd., commercial name: Himoloc ZP-700, and cation density: 6 mmol/g) was added to blend them, and they were heat-dried at 90° C. for 20 minutes. Thereafter, the resultant mixture was classified with a sieve having a mesh opening size of 850 µm, thus obtaining particles of not larger than 850 µm. These are named a water-absorbing agent (6). The various properties of the water-absorbing agent (6) as obtained are listed in Tables 2 and 3.

EXAMPLE 7

To 100 parts of the water-absorbent resin particles (A-1) as obtained in Referential Example 1, 10 parts of 10% aqueous solution of the cationic polymer compound (B-3) as obtained in Referential Example 5 was added to blend them, and they were heat-dried at 90° C. for 20 minutes. Thereafter, the resultant mixture was classified with a sieve having a mesh opening size of 850 μm, thus obtaining particles of not larger than 850 μm. These are named a water-absorbing agent (7). The various properties of the water-absorbing agent (7) as obtained are listed in Tables 2 and 3.

EXAMPLE 8

To 100 parts of the water-absorbent resin particles (A-1) as obtained in Referential Example 1, 10 parts of 10% aqueous solution of the cationic polymer compound (B-4) as obtained in Referential Example 5 was added to blend them, and they were heat-dried at 90° C. for 20 minutes. Thereafter, the resultant mixture was classified with a sieve having a mesh opening size of 850 μm, thus obtaining particles of not larger than 850 μm. These are named a water-absorbing agent (8). The various properties of the water-absorbing agent (8) as obtained are listed in Tables 2 and 3.

EXAMPLE 9

To 100 parts of the water-absorbent resin particles (A-1) as obtained in Referential Example 1, 10 parts of 5% aqueous solution of polyamidine (produced by HYMO Co., Ltd., commercial name; Himoloc ZP-700, and cation density: 6 mmol/g) was added to blend them, and they were heat-dried at 90° C. for 20 minutes. Thereafter, the resultant mixture was classified with a sieve having a mesh opening size of 850 μm, thus obtaining particles of not larger than 850 μm. To these particles, 0.5 part of silicon oxide of super-fine particle (produced by Nippon Aerosil Co., Ltd., commercial name: Aerosil 200) was further added to blend them. This is named a water-absorbing agent (9). The various properties of the water-absorbing agent (9) as obtained are listed in Tables 2 and 3.

EXAMPLE 10

To 100 parts of the water-absorbent resin particles (A-1) as obtained in Referential Example 1, 5 parts of 10% aqueous solution of partially hydrolyzed poly(N-vinylformamide) (produced by BASF, commercial name: Catio-fastPR8106, and cation density: 6.1 mmol/g) was added to blend them, and they were heat-dried at 90° C. for 20 minutes. Thereafter, the resultant mixture was classified with a sieve having a mesh opening size of 850 μm, thus obtaining particles of not larger than 850 μm. To these particles, 0.5 part of silicon oxide of super-fine particle (produced by Nippon Aerosil Co., Ltd., commercial name: Aerosil 200) was further added to blend them. This is named a water-absorbing agent (10). The various properties of the water-absorbing agent (10) as obtained are listed in Tables 2 and 3.

EXAMPLE 1

To 100 parts of the water-absorbent resin particles (A-1) as obtained in Referential Example 1, 7 parts of 10% aqueous solution of polyamidine (produced by Dia-Nitrix Co., Ltd., commercial name: PVAD-L, and cation density: 5.8 mmol/g) was added to blend them, and they were heat-dried at 90° C. for 20 minutes. Thereafter, the resultant mixture was classified with a sieve having a mesh opening size of 850 μm, thus obtaining particles of not larger than 850 μm. To these particles, 0.5 part of silicon oxide of super-fine particle (produced by Nippon Aerosil Co., Ltd., commercial name: Aerosil 200) was further added to blend them. This is named a water-absorbing agent (11). The various properties of the water-absorbing agent (11) as obtained are listed in Tables 2 and 3.

COMPARATIVE EXAMPLE 11

The water-absorbent resin particles (A-1) as obtained in Referential Example 1 were named a comparative water-absorbing agent (1). The various properties of the comparative water-absorbing agent (1) as obtained are listed in Tables 2 and 3.

COMPARATIVE EXAMPLE 2

To 100 parts of the water-absorbent resin particles (C-1) as obtained in Comparative Referential Example 1, 5 parts of 30% aqueous solution of polyethylenimine (number-average molecular weight: about 70,000 and produced by Nippon Shokubai Co., Ltd.) was added, thus obtaining a comparative water-absorbing agent (2). The various properties of the comparative water-absorbing agent (2) as obtained are listed in Tables 2 and 3.

COMPARATIVE EXAMPLE 3

To 100 parts of the water-absorbent resin particles (A-1) as obtained in Referential Example 1, 5 parts of the cationic polymer compound (D-1) as obtained in Comparative Referential Example 2 was added, thus obtaining a comparative water-absorbing agent (3). The various properties of the comparative water-absorbing agent (3) as obtained are listed in Tables 2 and 3.

COMPARATIVE EXAMPLE 4

To 100 parts of the water-absorbent resin particles (C-1) as obtained in Comparative Referential Example 1, 10 parts of 30% aqueous solution of ethylenediamine was added, and they were heat-dried at 90° C. for 20 minutes. Thereafter, the resultant mixture was classified with a sieve having a mesh opening size of 850 μm, thus obtaining particles of not larger than 850 μm. This is named a comparative water-absorbing agent (4). The various properties of the comparative water-absorbing agent (4) as obtained are listed in Tables 2 and 3.

COMPARATIVE EXAMPLE 5

To 100 parts of the water-absorbent resin particles (C-1) as obtained in Comparative Referential Example 1, 20 parts of 30% aqueous solution of polyethylenimine (number average molecular weight: about 70,000, produced by Nippon Shokubai Co., Ltd.) was added to blend them, and they were heat-dried at 120° C. for 10 minutes. Thereafter, the resultant mixture was classified with a sieve having a mesh opening size of 850 μm, thus obtaining particles of not larger than 850 μm. To these particles, 1 part of silicon oxide of super-fine particle (produced by Nippon Aerosil Co., Ltd., commercial name: Aerosil 200) was further added to blend them. This is named a comparative water-absorbing agent (5). The various properties of the comparative water-absorbing agent (5) as obtained are listed in Tables 2 and 3.

COMPARATIVE EXAMPLE 6

Making reference to Example 3 as described in JP-A-509591/1997, its tracing test was carried out in the following procedure:

To a Kitchen-type mixer, 100 g of the water-absorbent resin particles (C-2) as obtained in Comparative Referential Example 3 was added. A solution, which comprised 10 g of 10 weight % polyallylamine (commercial name: PAA-10C, weight-average molecular weight: about 10,000, produced by Nitto Boseki Co., Ltd, and cation density: 17.1 mmol/g) and 20 g of ethanol, was prepared. After a portion of the solution was sprayed onto the absorbent gel-formable particles with a spraying apparatus, the mixer was operated for about 4 minutes. The spraying and mixing procedure was repeated until the total of the solution was sprayed onto the absorbent gel-formable particles. The resultant mixture was dried under vacuum at 100° C. for about 3 hours. The resultant dried absorbent material was pulverized with a hammer pulverizer and classified with a standard #20-mesh sieve (850 μm), thus obtaining particles passing through the standard #20-mesh sieve. These are named a comparative water-absorbing agent (6). The various properties of the comparative water-absorbing agent (6) as obtained are listed in Tables 2 and 3.

COMPARATIVE EXAMPLE 7

Making reference to Example 2 as described in JP-A-3123/1997, its tracing test was carried out in the following procedure:

To 100 parts of the water-absorbent resin particles (C-2) as obtained in Comparative Referential Example 3, 5.5 parts of 43% hydrochloride solution (70 mol % neutralized product) of polyethylenimine (number-average molecular weight: about 70,000, and produced by Nippon Shokubai Co., Ltd.) was added to blend them, and they were kept in a hot-wind-dryer of 90° C. for 20 minutes after the blending. Thereafter, the resultant mixture was passed through a metal gauze having an opening size of 840 μm, thus obtaining a water-absorbing agent. This is named a comparative water-absorbing agent (7). The various properties of the comparative water-absorbing agent (7) as obtained are listed in Tables 2 and 3.

Figure 6:
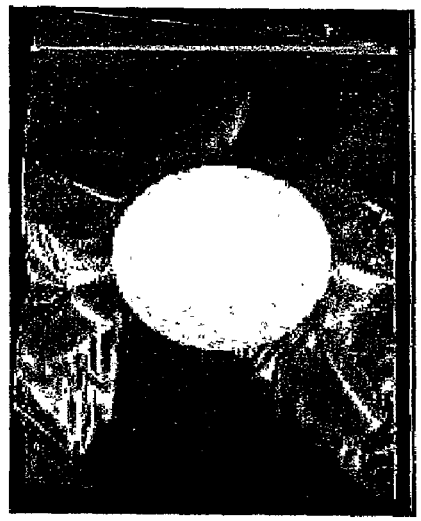
FIG. 6 shows image examples before and after pressurization when measuring the gel deformation under a load (16 hrPT) which is one of the properties as displayed by the water-absorbing agent in the present invention, and shows examples of swollen water-absorbing agent aggregates and deformed swollen water-absorbing agent aggregates as obtained after pressurization. Herein, a water-absorbing agent 1 is compared with a comparative water-absorbing agent 2.
Figure 6:
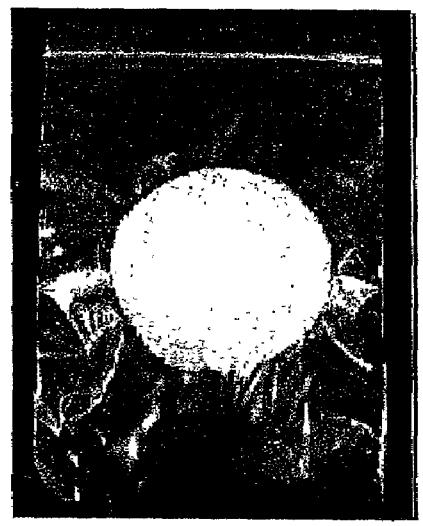
Figure 6:
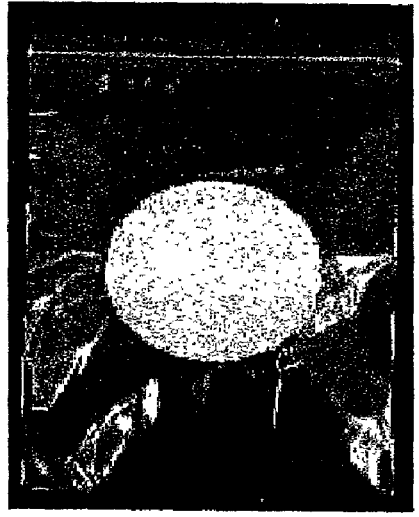
Figure 6:
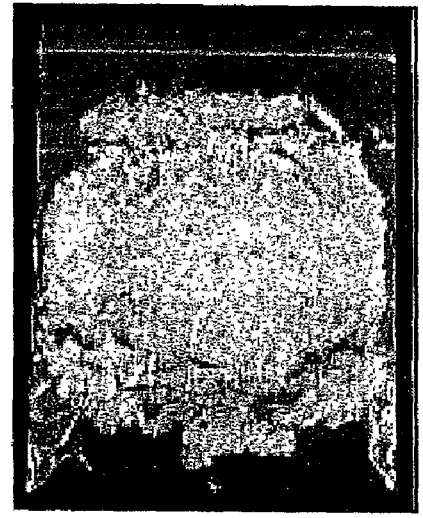

As is described in Tables, the water-absorbing agents as obtained in Examples exhibited a high GV and a high AAP, and an excellent 16 hrPT, 0.5 hrPT, BBS, 16 hrBBS, ΔPT, and DBBS. Among these, the water-absorbing agents as obtained by comprising the crosslinked cationic polymer compound as described in Examples 1 to 3, and as obtained by comprising the cationic polymer compound as described in Examples 6 to 11 are particularly excellent in the effects. In Comparative Example 1 as obtained in Comparative Examples, the water-absorbing agent was produced without blending the water-absorbing resin particles (A) and the cationic polymer compound (B) together. Therefore, its 16 hrPT, 0.5 hrPT, BBS, and 16 hrBBS were worse. In Comparative Examples 2 and 5 among the comparative water-absorbing agents, the water-absorbing agents do not have a sufficient AAP as a water-absorbing agent because the AAP of the water-absorbent resin particles as used are lower. In Comparative Examples 3 and 4, the water-absorbent resin particles as used exhibit a high GV and a high APP, but the cationic polymer as used is not favorable. Therefore, its 16 hrPT, 0.5 hrPT, BBS, and 16 hrBBS were worse. In Comparative Examples 6 and 7, the water-absorbent resin particles exhibit a low FRUP and a low SFC, and the cationic polymer compounds as used are not proper because they are not uncrosslinked. Therefore, the sufficient performance could not be obtained in 16 hrPT, 0.5 hrPT, BBS, and 16 hrBBS. FIG. 6 described photos of the water-absorbing agent 1 and the comparative water-absorbing agent 2 before or after pressurization when the 16 hrPT is measured. In the water-absorbing agent 1, the water-absorbing agent aggregate hardly deforms because it has an excellent shape-maintaining property. However, the shape of the comparative water-absorbing agent 2 was deformed.

In the above way, as is also apparent from Examples of the present invention, the water-absorbing agent and its production process according to the present invention provide: a novel water-absorbing agent of which the GV, AAP and SFC are also excellent, which has an excellent shape-maintaining property or BBS of a water-absorbing agent aggregate after swelling, and maintains the effects for a further long time after water is absorbed.

TABLE 1

| Water-absorbent resin particles (A) | GV (g/g) | AAP (g/g) | FRUP (second) | SFC* |
|---|---|---|---|---|
| A-1 | 25.6 | 22.4 | 70 | 101 |
| A-2 | 29.2 | 25.1 | 220 | 40 |
| C-1 | 34.1 | 8.2 | 2000 | 2 |
| C-2 | 28.2 | 21.3 | 1214 | 10 |

*Unit ($10^{-7} \times cm^3 \times s \times g^{-1}$)

TABLE 2

| | Water-absorbent resin particles (A) | Cationic polymer compound (B) | Water-absorbing agent | | |
|---|---|---|---|---|---|
| | | | Number | GV (g/g) | AAP (g/g) | 16 hr PT (cm) |
| Example 1 | A-1 | B-1 | (1) | 25.1 | 20.1 | 7.8 |
| Example 2 | A-1 | B-2 | (2) | 24.0 | 20.0 | 8.7 |
| Example 3 | A-2 | B-1 | (3) | 28.5 | 24.1 | 8.5 |
| Example 4 | A-1 | PAA-HCl | (4) | 25.0 | 22.0 | 12.0 |
| Example 5 | A-2 | PEI + Si | (5) | 26.1 | 20.5 | 8.0 |
| Example 6 | A-1 | PVAD | (6) | 25.2 | 21.0 | 7.9 |
| Example 7 | A-1 | B-3 | (7) | 25.4 | 22.1 | 9.5 |
| Example 8 | A-1 | B-4 | (8) | 25.3 | 21.5 | 8.5 |
| Example 9 | A-1 | PVAD + Si | (9) | 25.5 | 21.4 | 9.3 |
| Example 10 | A-1 | PR8106 | (10) | 25.2 | 21.1 | 9.9 |
| Example 11 | A-1 | PVAD-L | (11) | 25.3 | 21.0 | 9.0 |
| Comparative Example 1 | A-1 | None | Comparative (1) | 25.6 | 22.4 | 17.0 |
| Comparative Example 2 | C-1 | PEI | Comparative (2) | 28.5 | 7.6 | 15.0 |
| Comparative Example 3 | A-1 | D-1 | Comparative (3) | 24.9 | 23.0 | 17.0 |
| Comparative Example 4 | C-1 | EDA | Comparative (4) | 32.5 | 8.3 | 16.0 |
| Comparative Example 5 | C-1 | PEI + Si | Comparative (5) | 32.3 | 6.1 | 14.5 |
| Comparative Example 6 | C-2 | PAA | Comparative (6) | 27.5 | 21.1 | 15.7 |

TABLE 2-continued

| | Water-absorbent resin particles (A) | Cationic polymer compound (B) | Water-absorbing agent | | | |
|---|---|---|---|---|---|---|
| | | | Number | GV (g/g) | AAP (g/g) | 16 hr PT (cm) |
| Comparative Example 7 | C-2 | PEI-HCl | Comparative (7) | 27.3 | 19.0 | 10.8 |

PAA-HCl: Polyallylamine hydrochloride, PEI + Si: Polyethylenimine + Aerosil 200, PVAD: Polyamidine (produced by HYMO, commercial name: Himoloc ZP-700), PVAD + Si: Polyamidine + Aerosil 200, PR8106: Partially hydrolyzed poly(N-vinylformamide) (produced by BASF, commercial name: CatiofastPR8106), PVAD-L: Polyamidine (produced by Dia-Nitrix Co., Ltd., commercial name: PVAD-L), PAA: Polyallylamine, PEI: Polyethylenimine, EDA: Ethylenediamine, PEI-HCl: Polyethylenimine hydrochloride

TABLE 3

| | Water-absorbing agent | | | | | |
|---|---|---|---|---|---|---|
| | Number | SFC* | 0.5 hr PT (cm) | ΔPT (cm) | BBS (gf) | 16 hr BBS (gf) | DBBS (%) |
| Example 1 | (1) | 154 | 7.4 | 0.4 | 226 | 210 | 7.1 |
| Example 2 | (2) | 130 | 8.5 | 0.2 | 170 | 155 | 8.8 |
| Example 3 | (3) | 92 | 8.4 | 0.1 | 190 | 177 | 6.8 |
| Example 4 | (4) | 130 | 8.7 | 3.3 | 220 | 133 | 39.5 |
| Example 5 | (5) | 60 | 8.7 | −0.7 | 189 | 135 | 28.6 |
| Example 6 | (6) | 121 | 7.7 | 0.2 | 170 | 175 | −2.9 |
| Example 7 | (7) | 131 | 9.3 | 0.2 | 178 | 183 | −2.8 |
| Example 8 | (8) | 128 | 8.6 | −0.1 | 225 | 220 | 2.2 |
| Example 9 | (9) | 158 | 9.5 | −0.2 | 131 | 130 | 0.8 |
| Example 10 | (10) | 152 | 10.4 | −0.5 | 125 | 125 | 0.0 |
| Example 11 | (11) | 163 | 9.1 | −0.1 | 134 | 137 | −2.2 |
| Comparative Example 1 | Comparative (1) | 101 | 17.0 | 0.0 | 30 | 28 | 6.7 |
| Comparative Example 2 | Comparative (2) | 10 | 15.0 | 0.0 | 75 | 50 | 33.3 |
| Comparative Example 3 | Comparative (3) | 120 | 17.0 | 0.0 | 34 | 30 | 11.8 |
| Comparative Example 4 | Comparative (4) | 2 | 16.0 | 0.0 | 25 | 21 | 16.0 |
| Comparative Example 5 | Comparative (5) | 10 | 9.2 | 5.3 | 183 | 75 | 59.0 |
| Comparative Example 6 | Comparative (6) | 45 | 11.0 | 4.7 | 124 | 70 | 43.5 |
| Comparative Example 7 | Comparative (7) | 21 | 6.7 | 4.1 | 250 | 118 | 52.8 |

*Unit ($10^{-7} \times cm^3 \times s \times g^{-1}$)

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

The invention claimed is:

1. A water-absorbing agent, which comprises a polymer obtained by a process including the steps of polymerizing and then cross linking a monomer including acrylic acid and/or a salt thereof,
    with the water-absorbing agent being characterized by exhibiting a free swelling capacity of not less than 23 g/g (GV), an absorption capacity of not less than 20 g/g under a load of 4.9 kPa (AAP), and a gel deformation of not more than 12.5 cm under a load (16 hrPT).

2. A water-absorbing agent according to claim 1, which exhibits a deterioration of ball burst strength of not more than 40% (DBBS).

3. A water-absorbing agent according to claim 1, which exhibits a gel deformation deterioration of not more than 3.5 cm under a load with the passage of time (ΔPT).

4. A water-absorbing agent according to claim 1, which further comprises an inorganic powder.

5. A water-absorbent structure, which comprises the water-absorbing agent as recited in claim 1.

6. A water-absorbing agent according to claim 1, wherein said water-absorbing agent exhibits a saline flow conductivity of not less than 50 ($10^{-7} \times cm^3 \times s \times g^{-1}$) (SFC).

7. A water-absorbing agent, which comprises a polymer obtained by a process including the steps of polymerizing and then crosslinking a monomer including acrylic acid and/or a salt thereof,
    with the water-absorbing agent being characterized by exhibiting a free swelling capacity of not less than 23 g/g (GV), an absorption capacity of not less than 20 g/g under a load of 4.9 kPa (AAP), and a 16 hours' ball burst strength of not less than 80 gf (16 hrBBS).

8. A water-absorbing agent according to claim 7, which exhibits a deterioration of ball burst strength of not more than 40% (DBBS).

9. A water-absorbing agent according to claim 7, which exhibits a gel deformation deterioration of not more than 3.5 cm under a load with the passage of time (ΔPT).

10. A water-absorbing agent according to claim 7, which further comprises an inorganic powder.

11. A water-absorbent structure, which comprises the water-absorbing agent as recited in claim 7.

12. A water-absorbing agent according to claim 7, wherein said water-absorbing agent exhibits a saline flow conductivity of not less than 50 ($10^{-7} \times cm^3 \times s \times g^{-1}$) (SFC).

13. A water-absorbing agent, which comprises a polymer obtained by a process including the steps of polymerizing and then crosslinking a monomer including acrylic acid and/or a salt thereof,
    with the water-absorbing agent being characterized by exhibiting a free swelling capacity of not less than 23 g/g (GV), a gel deformation of not more than 12.5 cm under a short-time load (0.5 hrPT), and a gel deformation deterioration of not more than 3.5 cm under a load with the passage of time (ΔPT).

14. A water-absorbing agent according to claim 13, which exhibits an absorption capacity of not less than 20 g/g under a load of 4.9 kPa (AAP).

15. A water-absorbing agent according to claim 13, which exhibits a gel deformation of not more than 12.5 cm under a load (16 hrPT).

16. A water-absorbing agent according to claim 13, which exhibits a 16 hours' ball burst strength of not less than 80 gf (16 hrBBS).

17. A water-absorbing agent according to claim 13, which further comprises an inorganic powder.

18. A water-absorbent structure, which comprises the water-absorbing agent as recited in claim 13.

19. A water-absorbing agent according to claim 13, wherein said water-absorbing agent exhibits a saline flow conductivity of not less than 50 ($10^{-7} \times cm^3 \times s \times g^{-1}$) (SFC).

20. A water-absorbing agent, which comprises a polymer obtained by a process including the steps of polymerizing and then crosslinking a monomer including acrylic acid and/or a salt thereof,
    with the water-absorbing agent being characterized by exhibiting a free swelling capacity of not less than 23 g/g (GV), a ball burst strength of not less than 80 gf (BBS), and a deterioration of ball burst strength of not more than 40% (DBBS).

21. A water-absorbing agent according to claim 20, which exhibits an absorption capacity of not less than 20 g/g under a load of 4.9 kPa (AAP).

22. A water-absorbing agent according to claim 20, which exhibits a gel deformation of not more than 12.5 cm under a load (16 hrPT).

23. A water-absorbing agent according to claim 20, which exhibits a 16 hours' ball burst strength of not less than 80 gf (16 hrBBS).

24. A water-absorbing agent according to claim 20, which further comprises an inorganic powder.

25. A water-absorbent structure, which comprises the water-absorbing agent as recited in claim 20.

26. A water-absorbing agent according to claim 20, wherein said water-absorbing agent exhibits a saline flow conductivity of not less than 50 ($10^{-7} \times cm^3 \times s \times g^{-1}$) (SFC).

* * * * *